United States Patent
Stone et al.

(10) Patent No.: US 7,329,773 B2
(45) Date of Patent: Feb. 12, 2008

(54) PROCESS FOR PRODUCING CARBAMOYLOXY (METH) ACRYLATES AND NEW CARBAMOYLOXY (METH)ACRYLATES

(75) Inventors: Vincent Stone, Brussels (BE); Jurgen Van Holen, Ghent (BE); Hugues Van Den Bergen, Drogenbos (BE)

(73) Assignee: Surface Specialties, S.A., Brussels (BE)

( * ) Notice: Subject to any disclaimer, the term of this patent is extended or adjusted under 35 U.S.C. 154(b) by 371 days.

(21) Appl. No.: 10/536,017

(22) PCT Filed: Nov. 18, 2003

(86) PCT No.: PCT/EP03/12887

§ 371 (c)(1),
(2), (4) Date: May 20, 2005

(87) PCT Pub. No.: WO2004/052843

PCT Pub. Date: Jun. 24, 2004

(65) Prior Publication Data

US 2006/0058549 A1    Mar. 16, 2006

(30) Foreign Application Priority Data

Dec. 12, 2002  (EP) ................................ 02027835

(51) Int. Cl.
*C07C 269/00* (2006.01)

(52) U.S. Cl. ...................................... 560/157; 560/158

(58) Field of Classification Search .................... None
See application file for complete search history.

(56) References Cited

U.S. PATENT DOCUMENTS

| 3,674,838 A | 7/1972 | Norstrom |
| 4,126,747 A | 11/1978 | Cowherd, III et al. |
| 4,956,264 A | 9/1990 | Geissler et al. |
| 5,043,363 A | 8/1991 | Noguchi et al. |

FOREIGN PATENT DOCUMENTS

| EP | 0 468 643 A |   | 1/1992 |
| JP | 06-298716 | * | 10/1994 |
| JP | 2001-040039 | * | 2/2001 |
| WO | 94 25537 A |   | 11/1994 |

* cited by examiner

*Primary Examiner*—Paul A. Zucker
(74) *Attorney, Agent, or Firm*—Wenderoth, Lind & Ponack, L.L.P.

(57) ABSTRACT

The invention relates to a process for producing carbamoyloxy (meth)acrylates which comprises transesterification of hydroxyalkyl carbamates with an (meth)acrylate of formula $CH_2\!=\!CR^{29}\!-\!COOR^{30}$ wherein $R^{29}$ is hydrogen or methyl and $R^{30}$ represents an alkyl group comprising from 1 to 8 carbon atoms, in the presence of an organotitanate, an organozirconate catalyst or an organotin catalyst, the carbamoyloxy (meth)acrylates thereby obtained and their use in radiation curable compositions.

19 Claims, No Drawings

PROCESS FOR PRODUCING CARBAMOYLOXY (METH) ACRYLATES AND NEW CARBAMOYLOXY (METH)ACRYLATES

The present invention relates to a process for producing carbamoyloxy (meth)acrylates and to new carbamoyloxy (meth)acrylates thereby obtained. The invention also relates to the uses of such compounds, especially in radiation curable compositions.

Radiation curable compositions have found a wide range of applications in numerous, fields, for example as coatings, varnishes and paints for protecting and decorating the most diverse substrates such as glass, metals, plastics, paper, as printing varnishes and inks or as adhesives for laminates, and the like. Because of the high viscosity of radiation curable oligomers or prepolymers used in radiation curable compositions, diluents are generally added in these compositions. In order to retain the advantage of radiation curing, so-called "reactive diluents" are used, permitting to eliminate the presence of solvents. These reactive diluents are generally low molecular weight compounds bearing one or more reactive carbon-carbon double bond, permitting them to be incorporated in the final polymer coating. These reactive diluents should have the following properties: low toxicity and irritancy, low volatility and odour, low viscosity, high reactivity. Moreover, they should be colorless and they should be able to preserve the performance integrity of the oligomers and prepolymers.

Current commercial available reactive diluents never completely fulfil all these prerequisites at the same time. Low molecular weight (meth)acrylates bearing carbamate groups are known as reactive diluents presenting one of the best compromises of the above-required properties. However, their properties and more specific properties such as adhesion on difficult substrates, pencil hardness and abrasion resistance, could still be improved. One of the best carbamoyloxy (meth)acrylates used in the art is n-butyl acryloyloxy ethyl carbamate.

Different processes have been disclosed for the synthesis of carbamoyloxy (meth)acrylates able to be used as reactive diluents in radiation curable compositions. U.S. Pat. No. 3,674,838 describes their synthesis by the so-called chloroformate method using phosgene as raw material and by the so-called urea method which need to be conducted at high temperatures, leading to an uncontrolled radical polymerization of the (meth)acrylates. U.S. Pat. No. 3,674,838 further mentions that carbamoyloxy (meth)acrylates could be synthesized via a transesterification reaction under conditions well known in the art. However, U.S. Pat. No. 4,126,747 teaches that methods using typical transesterifcation catalysts produces commercially unacceptable yields of desired carbamoyloxy (meth)acrylates and that these products are highly colored. U.S. Pat. No. 4,126,747 further describes a direct esterification process using (meth)acrylic acid. B. M. Culbertson, H. J. Langer, L. K Post, Org. Coat Plast. Chem. (1979). 40, 903-8, describes the so-called isocyanate method to make monofunctional (meth)acrylic monomers containing carbamate functionality by treating hydroxyalkyl(meth)acrylates with equimolar amounts of various isocyanates. Currently used industrial process for making n-butyl acryloyloxy ethyl carbamates based on the isocyanate method.

These known processes, and especially the chloroformate and isocyanate methods, for making known carbamoyloxy acrylates or methacrylates use highly toxic and dangerous raw materials, such as low molecular weight isocyanates and phosgene. Storing, handling and processing these toxic raw materials at large scale can only occur with highly expensive secured industrial equipments and safety procedures in an adapted industrial environment. Moreover, the reactions involved in these methods being highly exothermic, risk for runaway reactions leading to polymerization in the reactor and atmospheric pollution with toxic materials is important at large scale. Another major drawback of the known processes, and especially of the isocyanate method, is that it may lead to products containing significant amounts of toxic impurities, for example aliphatic isocyanates, such as butyl isocyanate, and/or low molecular weight hydroxyalkyl acrylates, such as hydroxyethyl acrylate. The legislation on toxic impurities calls for the need of processes that are able to lead to products free of such impurities or containing these impurities in very low concentrations, typically below 1000 ppm. Moreover, these processes generally lead to relative low yields so that highly expensive purification processes are needed. They also lead to highly colored products that precludes their use in some applications such as overprint varnishes. The direct esterification method described in U.S. Pat. No. 4,126,747 presents the disadvantage to produce a relative low yield so that a large amount of non-(meth) acrylated hydroxycarbamate is still present in the final product which may have a detrimental effect on the diluting power of the product due to its relative high viscosity and which may lead to migration problems in the cured coatings. Another problem with this direct esterification method is that high concentrations of acidic catalyst is needed, which in general triggers side reactions leading directly or indirectly to the formation of toxic by-products (such as hydroxyethyl acrylate) and which also causes problems with corrosion and for elimination of catalyst residues. Another drawback of this direct esterification method is that high excess in (meth)acrylic acid is needed which requires efficient recycling procedures.

Higher molecular weight carbamoyloxy (meth)acrylates are also the subject of this invention. Being of higher viscosity, the latter structures can be used as an oligomer in radiation curable formulations. The two approaches applied to make the current commercially available oligomers bearing carbamate groups (often referred to as "urethane (meth) acrylates") make use of aliphatic or aromatic multifunctional (mostly difunctional) isocyanates. The first approach makes use of the above mentioned isocyanate method: multifunctional isocyanates are reacted with hydroxyfunctional (meth)acrylate monomers like hydroxyethyl (meth)acrylate, hydroxypropyl (meth)acrylate or pentaerythritol tri(meth) acrylate. In a second approach, this isocyanate method is modified to enlarge the range of accessible structures. A portion of the hydroxyfunctional (meth)acrylate monomers is replaced by other structures having OH groups such as polyols (such as ethylene glycol, glycerol or hexanediol), polyester polyols (such as hexanediol/adipic acid OH-terminated polyester) or polyether polyols (such as polyethyleneglycol, polypropyleneglycol). Both approaches being based on the above isocyanate method, both present the same above process-related drawbacks. Moreover, for a given molecular weight and (meth)acrylate functionality, urethane (meth)acrylates obtained by these methods are known to show a high viscosity as compared to the other oligomers used in radiation curable formulations, one of the main reasons being the strong hydrogen bonding involving the protons of the carbamate groups. In the second approach, every supplemental (meth)acrylate group in the molecule implies the presence of two supplemental urethane groups if a diisocyanate is used. In other words, viscosity will increase very much with (meth)acrylate functionality. This leads to the facts that the urethane (meth)acrylates obtained by this approach will have to be of limited (meth)acrylate functionality (typically ≦3) and/or will often have to be diluted with an (meth)acrylate monomer at the end of their synthesis to remain tractable when they will have to be formulated. Furthermore, radiation-curable formulations will always have to contain a limited amount of urethane (meth)acrylate(s) and high amounts of reactive diluents in order to have a viscosity compatible with industrial application equipments. Due to these limitations, specific coating properties that can only be achieved by use of urethane (meth)acrylates, can thus often not be maximized. The need for high amounts of irritant and sensitizing reactive diluents precludes the use of urethane (meth)acrylates in certain applications where the viscosity of the formulation should be very low (e.g. spray coatings).

The present invention aims to find an improved process that overcomes these problems.

The present invention provides a process for producing carbamoyloxy (meth)acrylates which comprises the transesterification of an hydroxyalkyl carbamate of formula (I), (II), (III), (IV), (V), (VI) or (VII)

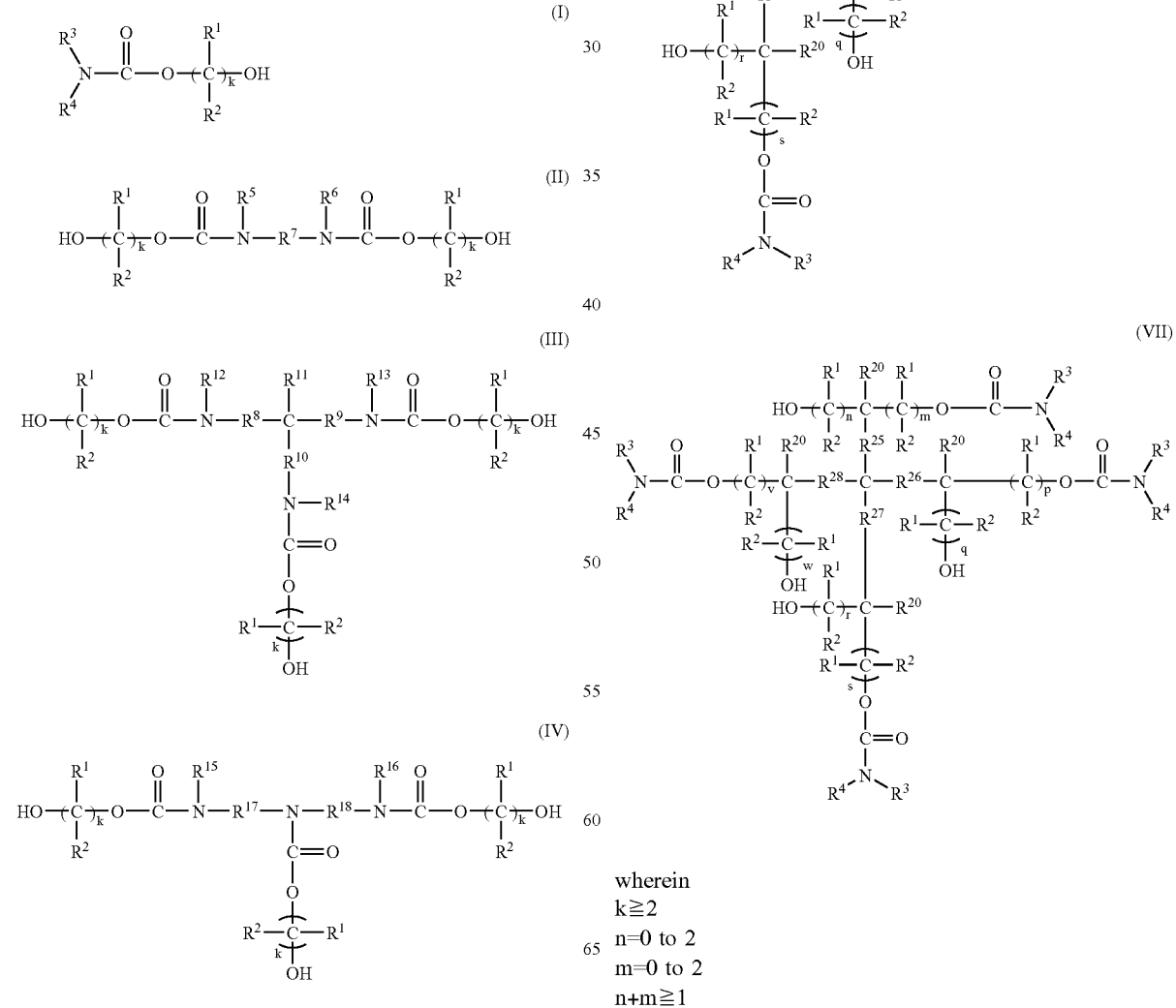

wherein
k≧2
n=0 to 2
m=0 to 2
n+m≧1

$p=n$ or $m$, $q=n$ or $m$, $r=n$ or $m$, $s=n$ or $m$, $v=n$ or $m$, $w=n$ or $m$ $(p+q)=(r+s)=(v+w)=(n+m)$ each $R^1$, each $R^2$, each $R^{20}$ is, independently, chosen from the group of
- hydrogen,
- halogen,
- hydroxy,
- alkyl, optionally substituted by hydroxy; halogen; aryl and/or aryl substituted by hydroxy, halogen or alkyl; and optionally containing from 1 to 8 ether bridges,
- alkenyl, optionally substituted by hydroxy; halogen; aryl and/or aryl substituted by hydroxy, halogen or alkyl; and optionally containing from 1 to 8 ether bridges,
- aryl, optionally substituted by hydroxy; halogen; alkyl; alkyl substituted by hydroxy, halogen and/or aryl; and/or alkyl containing from 1 to 8 ether bridges, $R^3$ is an alkyl, optionally substituted by hydroxy, tertiary amine and/or aryl, and optionally containing from 1 to 20 ether bridges and/or from 1 to 3 tertiary amine bridges, $R^4$, $R^5$, $R^6$, $R^{12}$, $R^{13}$, $R^{14}$, $R^{15}$ and $R^{16}$ are, independently, chosen from the group of
- hydrogen, and
- alkyl, optionally substituted by hydroxy, tertiary amine and/or aryl, and optionally containing from 1 to 8 ether bridges and/or from 1 to 3 tertiary amine bridges,
with the proviso that, respectively, $R^3$ and $R^4$, $R^5$ and $R^6$, $R^{12}$ and/or $R^{13}$ and/or $R^{14}$, $R^{15}$ and $R^{16}$ may be linked together in order to form a ring, $R^7$, $R^8$, $R^9$, $R^{10}$, $R^{17}$ and $R^{18}$ are, independently, chosen from alkylene, alkenylene, arylene and aralkylene chains which may contain from 1 to 8 ether bridges and/or from 1 to 3 tertiary amine bridges, $R^{11}$ is hydrogen or alkyl;

$R^{19}$, $R^{21}$, $R^{22}$, $R^{23}$, $R^{25}$, $R^{26}$, $R^{27}$ and $R^{28}$, are, independently, chosen from alkylene, alkenylene, arylene and aralkylene chains which may contain from 1 to 20 ether bridges, from 1 to 4 tertiary amine bridges, from 1 to 4 —CO— bridges and/or from 1 to 4 —O—CO— bridges;

A is

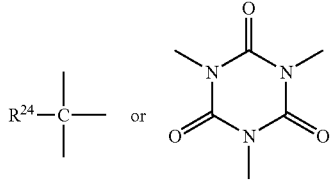

wherein $R^{24}$ is hydrogen or alkyl;
with a (meth)acrylate of formula (VIII)

$$CH_2=CR^{29}-COOR^{30} \qquad (VIII)$$

wherein $R^{29}$ is hydrogen or methyl, and $R^{30}$ represents an alkyl group comprising from 1 to 8 carbon atoms; in an equivalent ratio of (meth)acrylate to hydroxylalkyl carbamate higher than 3.5 and in the presence of an organotitanate, an organozirconate or an organotin catalyst.

The term "alkyl", as used herein, is defined as including saturated, monovalent hydrocarbon radicals having straight, branched or cyclic moieties or combinations thereof and containing 1 to 50 carbon atoms.

The term "alkenyl" as used herein, is defined as including straight and cyclic, branched and unbranched, unsaturated hydrocarbon radicals having at least one double bond and containing from 2 to 50 carbon atoms; such as ethenyl (=vinyl), 1-methyl-1-ethenyl, 2-methyl-1-propenyl, 1-propenyl, 2-propenyl (=allyl), 1-butenyl, 2-butenyl, 3-butenyl, 4-pentenyl, 1-methyl-4-pentenyl, 3-methyl-1-pentenyl, 1-hexenyl, 2-hexenyl, and the like.

The term "aryl" as used herein, is defined as including an organic radical derived from an aromatic hydrocarbon comprising 1 or more rings by removal of one hydrogen, and containing from 5 to 30 carbon atoms, such as phenyl and naphthyl.

The term "alkoxy", as used herein, is defined as —O-alkyl groups wherein "akyl" is as defined above.

The term "alkylene" as used herein, is defined as including saturated, divalent hydrocarbon radicals having straight, branched or cyclic moieties or combinations thereof and containing 1 to 50 carbon atoms.

The term "alkenylene" as used herein, is defined as including unsaturated, divalent hydrocarbon radicals having straight, branched or cyclic moieties or combinations thereof, containing at least one carbon-carbon double bond and containing 1 to 50 carbon atoms.

The term "arylene" as used herein, is defined as including divalent radicals derived from an aromatic hydrocarbon comprising one or more rings by removal of two hydrogen atoms and containing from 5 to 30 carbon atoms.

The term "aralkylene" as used herein, represents a divalent radical comprising a combination of alkylene and arylene moieties.

By alkyl, alkenyl, alkylene, alkenylene, arylene and aralkylene containing an ether bridge is meant an alkyl, alkenyl, alkylene, alkenylene, arylene or aralkylene radical wherein a carbon atom is replaced by an oxygen atom, forming a group such as —C—O—C—.

By alkyl, alylene, alkenylene, arylene and aralkylene chain containing tertiary amine bridge is meant such radical wherein a tertiary amine group is present between 2 carbon atoms, forming a group of formula —C—NR—C—, wherein R represents an alkyl or aryl group. In that case, R is preferably an alkyl group containing from 1 to 15 carbon atoms.

By alkylene, alkenylene, arylene and aralkylene containing a —CO—O— bridge is meant an alkylene, alkenylene, arylene or aralkylene radical wherein a

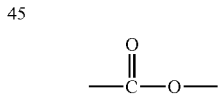

group is present between 2 carbon atoms, forming a group of formula

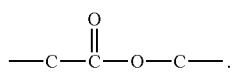

By alkylene, alkenylene, arylene and aralkylene containing a —CO— bridge is meant an alkylene, alkenylene, arylene or aralkylene radical wherein a

group is present between 2 carbon atoms.

The transesterification reaction in the process according to the invention is preferably effectuated at temperatures of at least 40° C., more preferably of at least 50° C., and most preferably of at least 60° C. The transesterification reaction is generally effectuated at a temperature of at most 110° C., more preferably of at most 105° C. When hydroxyalkyl carbamates bearing only primary hydroxy group(s) such as those wherein $R^1$ and $R^2$ on the same carbon atom as the —OH are hydrogen, and alkyltitanate catalysts, are used, the temperature at which the transesterification reaction is conducted is more preferably of at most 75° C., and most preferably of at most 70° C.

The maintenance of the temperature during the transesterification reaction can be done by any means known therefore. The maintenance of the temperature is preferably achieved by distilling off, in general under reduced pressure, the azeotrope formed by the (meth)acrylate of formula (VIII) with its corresponding alcohol which is formed during the reaction.

The catalyst used in the transesterification reaction can be an organotin catalyst. The organotin catalyst is preferably chosen from dibutyltin oxide, monobutyltin oxide, monobutyltindihydroxychloride, n-butyl tin tris(2-ethylhexanoate), dibutyltindilaurate, dioctyltindilaurate, dibutyltinmaleate, dibutyltindiacetate, dibutyltindiisooctoate, dibutyltincarboxylate, dimethyltindichloride, and their mixtures; it is most preferably dibutyltindilaurate and/or dioctyltindilaurate.

The catalyst used in the transesterification reaction is preferably an organotitanate catalyst. The organotitanate catalyst is preferably chosen from alkyltitanates, more particularly from tetraalkyltitanates, wherein each alkyl, independently, comprises from 2 to 8 carbon atoms. More preferred are isopropyltitanate, n-butyltitanate, ethyltitanate, n-propyltitanate, 2-ethylhexyltitanate and their mixtures. Particularly preferred are isopropyltitanate, n-butyltitanate and their mixtures.

The catalyst used in the transesterification reaction is most preferably an organozirconate catalyst. The latter is preferably chosen from zirconium acetate, zirconium acetylacetonate, zirconium hexafluoroacetylacetonate, zirconium trifluoroacetylacetonate, zirconium propionate, zirconium 2-ethylhexanoate, zirconium t-butoxide, zirconium n-butoxide, zirconium ethoxide, zirconium n-propoxide, zirconium isopropoxide, zirconium chloride, zirconium bromide, zirconium fluoride, zirconium iodide, zirconium oxychloride, zirconium hydrochloride, zirconium methacrylate and their mixtures; it is most preferably zirconium acetylacetonate and/or zirconium n-butoxide.

The organozirconate catalyst is preferably chosen from alkylzirconates, more particularly from tetraalkylzirconates, wherein each alkyl, independently, comprises from 2 to 8 carbon atoms and from zirconium 1,3-diketone chelates, and their mixtures.

As described in FR2747675 (Elf Atochem SA), any of these zirconium catalysts can be doped with β-diketones (e.g. acetylacetone), esters of ketonic acid (e.g. ethylacetoacetate) or β-hydroxydiketones (e.g. hydroxybenzophenone).

The organozirconium catalyst is most preferably chosen from alkylzirconates, especially zirconium n-butoxide, in combination with zirconium acetylacetonate and/or a β-diketone, especially acetylacetone.

The amount of catalyst used in the transesterification reaction according to the invention, is preferably such that the weight ratio of catalyst to the generated carbamoyloxy (meth)acrylate is at least 0.003, preferably at least 0.005. The weight ratio does preferably not exceed 0.1, most preferably not 0.09. A too low concentration in catalyst could lead to unacceptable yields of the desired carbamoyloxy (meth)acrylate; higher concentrations could lead to the formation of undesirable side products and/or could influence the properties of the final product, necessitating or complicating its removal.

Although not absolutely required, residual catalyst may be removed from the reaction mixture obtained after the transesterification reaction. Organotin catalysts may be removed by one of the methods known in the art. Methods to get rid of tin catalysts from organic media relies either on adding a reagent that makes them insoluble in the matrix or washing methods by hydrolytic treatments. Organotitanate and organozirconate catalysts can be easily removed by adding any substance (polyol, water, . . . ) able to react with this catalyst and forming an insoluble precipitate that can be removed from the reaction mixture.

In a preferred embodiment of the process according to the invention, the reaction mixture obtained after the transesterification reaction is treated with water. The quantity of water used is preferably in the range of 0.1 to 5 g, most preferably from 0.5 to 3 g, per g of catalyst present in the reaction mixture. The treatment with water is preferably done under agitation, during 10 to 120 minutes, most preferably during 30 to 90 minutes. This treatment is preferably done at a temperature of 60 to 80° C. Titanium hydrolyzates being generally totally insoluble in the reaction mixture, they can easily be filtrated out by through standard filtration procedures. Zirconium hydrolyzates being generally soluble in the water phase, they can be extracted by water treatment.

In another preferred embodiment of the process according to the invention, the reaction mixture obtained after the transesterification reaction is treated with a polyol that, after reaction with the catalyst, can form a precipitate. For convenience of use, the polyol is preferably liquid in standard conditions. Useful polyols are ethylene glycol, alkoxylated pentaerythritols, alkoxylated trimethylolpropane, alkoxylated neopentyl glycol, glycerol. Most preferred polyol is glycerol. The quantity of polyol used is preferably such that the equivalent ratio of polyol to organotitanate is higher than 1 and lower than 1.3. By equivalent ratio of polyol to organotitanate is understood the number of equivalents of OH present in the polyol to the number of equivalent of alkyl groups present in the organotitanate catalyst. The treatment with polyol is preferably done under agitation, during 10 to 120 minutes, most preferably during 30 to 90 minutes. This treatment is preferably done at a temperature of 60 to 80° C. When reaction products are of high viscosity (typically >1000 mPa·s), it has been found that the titanium precipitate obtained by this way can be sometimes more easily filtrated than by using water.

When left in the reaction mixture, the catalyst is preferably immobilized on a polymer or reacted with a radically polymerizable compound. This precludes leaching phenomena in the end application.

While it is generally preferred not to use any solvent for the transesterification reaction, the latter may be used, for example, in order to improve the compatibility of a reagent or a catalyst so that the reaction mixture is homogeneous throughout the reaction.

The amount of (meth)acrylate of formula (VIII) used in the transesterification reaction according to the invention, Is such that the equivalent ratio of (meth)acrylate to hydroxyalkyl carbamate is higher than 3.5. By equivalent ratio of (meth)acrylate to hydroxyalkyl carbamate is understood the number of equivalents of (meth)acrylate to the number of equivalents of hydroxy groups present in the hydroxyalkyl carbamate. The equivalent ratio is preferably at least 4, more preferably at least 4.5. The equivalent ratio does preferably not exceed 10, most preferably not 8. A too low amount in (meth)acrylate leads to unacceptable yields of desired carbamoyloxy (meth)acrylate.

A part of the excess (meth)acrylate is preferably continuously distilled as an azeotrope with the corresponding alcohol formed during the transesterification reaction. The remaining part of the excess may be removed at the end of the transesterification reaction by concentration/stripping under vacuum, preferably under injection of air in order to prevent polymerization. This remaining part of the excess is preferably removed after removal of the residual catalyst.

The transesterification reaction is usually conducted in the presence of at least one polymerization inhibitor. By polymerization inhibitor is understood an additive which slows or inhibits the polymerization of the reactives and/or the formed products.

The transesterification reaction is preferably done in the presence of at least one polymerization inhibitor chosen from sterically hindered phenol derivatives. By sterically hindered phenol derivative is meant to designate a molecule containing a phenyl ring bearing at least one hydroxy group (—OH) and wherein at least one substituent other than hydrogen is present in ortho position of the —OH group on the phenyl ring. Preferred are sterically hindered phenol derivatives wherein a sustituent other than hydrogen is present in each ortho positions of the —OH group, i.e. o,o'-disubstituted phenols. In this case, both substituents may be the same or different. The substituent present in ortho of the —OH group is preferably an alkyl group, most preferably containing from 1 to 20 carbon atoms. The sterically hindered phenol derivative may contain different phenol moieties. Preferred sterically hindered phenol derivatives are chosen from the group of 2,6-di-tert-butyl-4-methylphenol (BHD, 2,6-dimethylphenol, 2,2'-methylenebis(4-methyl-6-(1-methyl-cyclohexyl) phenol), 2,2'-methylenebis(4-methyl-6-tert-butylphenol), 2,2'-methylenebis(4-ethyl-6-tert-butylphenol), 2,4-dimethyl-6-(1-methylpentadecyl)-phenol, alpha-tocopherol (vitamin E) and their mixtures.

The amount of sterically hindered phenol derivative present during the transesterification reaction is in general at least 100 ppm w/w, preferably at least 300 ppm w/w based on the quantity of carbamoyloxy (meth)acrylate formed. The amount of sterically hindered phenol derivative preferably does not exceed 5000 ppm w/w, most preferably not 3000 ppm w/w based on the quantity of final product formed.

Instead of, or in addition to, the sterically hindered phenol derivatives, other phenolic inhibitors may be added during the transesterification reaction. In a preferred embodiment of the process according to the invention, less than 1000 ppm, preferably less than 100 ppm, w/w based on the quantity of carbamoyloxy (meth)acrylate formed phenolic polymerization inhibitor other than the sterically hindered phenol derivatives, i.e. phenolic derivatives wherein the positions in ortho of the —OH group are hydrogen, are added to the reaction mixture.

Instead of, or in addition to, the sterically hindered phenol derivatives, other non-phenolic polymerization inhibitors may be added during the transesterification reaction. In this case, the amount of these non-phenolic polymerization inhibitors is preferably at least 100 ppm w/w based on the quantity of carbamoyloxy (meth)acrylate formed. In general, this amount does not exceed 900 ppm, preferably not 500 ppm w/w based on the quantity of final product formed. Preferred other polymerization inhibitors are chosen from phenothiazine, triphenylstibine, triphenylphosphine, quinones (such as para- benzoquinone), nitrones, nitro- and nitroso compounds (such as nitrobenzene), stable radicals (such as 2,2,6,6-tetramethyl-1-piperidinyloxy and diphenylpicrylhydrazil). Most preferred non-phenolic inhibitor is phenothiazine.

In the (meth)acrylates of formula (VIII) used in the process according to the invention, $R^{30}$ is preferably an alkyl comprising from 1 to 4 carbon atoms, most preferably, methyl, ethyl or n-butyl.

The hydroxyalkyl carbamates of formula (I), (II), (III), (IV), (V), (VI) and (VII) used in the process according to the invention may be obtained by any method suitable therefore.

Hydroxyalkyl carbamates of formula (I), (II), (III) and (IV) are preferably obtained by reacting amines of, respectively, formula (IX), (X), (XI) and (XII)

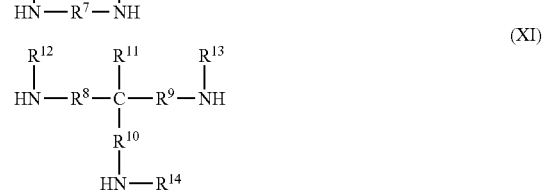

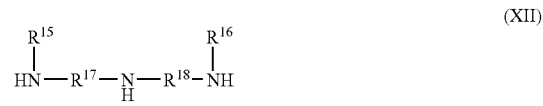

wherein $R^3$, $R^4$, $R^5$, $R^6$, $R^7$, $R^8$, $R^9$, $R^{10}$, $R^{11}$, $R^{12}$, $R^{13}$, $R^1$ $R^{18}$, are defined as here above, with a cyclic carbonate of formula (XIII)

wherein $R^1$, $R^2$ and k are defined as here above.

Hydroxyalkyl carbamates of formula (V), (VI) and (VII) are preferably obtained by reacting an amine of formula (IX)

wherein $R^3$ and $R^4$ are defined as here above, with, respectively, a cyclic carbonate of formula (XIV), (XV) and (XVI)

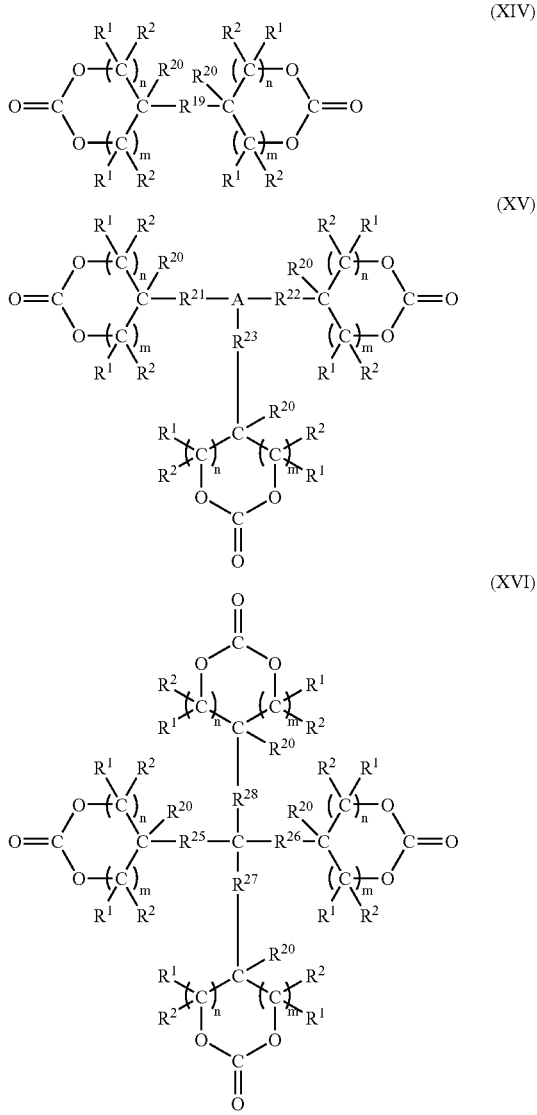

wherein $R^1$, $R^2$, $R^{19}$, $R^{20}$, $R^{21}$, $R^{22}$, $R^{23}$, $R^{24}$, $R^{25}$, $R^{26}$, $R^{27}$, $R^{28}$, A, n and m are defined as here above.

The preparation of the hydroxyalkyl carbamates by the above mentioned processes is exothermic. Therefore, the reaction temperature is preferably controlled in order to avoid side reactions which could give toxic by-products or which could lead to products which form toxic by-products further in the process according to the invention. During the preparation processes, the temperature is in general maintained below 100° C., preferably between 40 and 90° C. and most preferably between 50 and 80° C. When a primary amine is used, the reaction may be so exothermic that it is difficult to maintain the reaction mixture within the above temperature range. It is then preferred to add the cyclic carbonate to the amine in order to have a better control of the reaction temperature.

During the preparation of the hydroxyalkyl carbamates, the reaction mixture is preferably sparged with nitrogen. This sparging with nitrogen helps to avoid moisture that can lead to hydrolysis of the cyclic carbonate catalyzed by the amine. Sparging with nitrogen can also help in reducing the color of the hydroxyalkyl carbamate, especially when readily oxidized amines are used such as secondary amines or amines with ether groups. Alternatively or in addition to the sparging with nitrogen, an antioxidant may be used during the preparation of the hydroxyalkyl carbamates. Preferred antioxidants are aromatic phosphates, most preferred are triphenylphosphite or trisnonylphenylphosphite. The amount of these antioxidants is preferably at least 300 ppm w/w based on the quantity of hydroxyalkyl carbamate formed. In general, this amount does not exceed 5000 ppm, preferably not 2000 ppm w/w based on the quantity of hydroxyalkyl carbamate formed.

During the preparation of the hydroxyalkyl carbamates, the equivalent ratio amine to cyclic carbonate is preferably of 1.01 to 1.1 and most preferably, of 1 to 1.05. The equivalent ratio amine to cyclic carbonate is meant to designate the number of primary and secondary amine groups of the amine of formula (IX), (X), (XI) or (XII) per number of cyclic carbonate groups present in the cyclic carbonates of formula (XIII), (XIV), (XV) or (XVI) used. Especially when the boiling point of the amine is lower than 100° C. so that it can be stripped off the reactor under vacuum below this temperature, it is preferred working with an amine excess to so as speeding up the reaction. This is especially true for secondary amines with which reaction times are typically longer due to steric hindrance around the opening proton.

During the preparation of the hydroxyalkyl carbamates, a catalyst can be used. Secondary, higher molecular weight primary or hindered primary amines may lead to very slow ring opening reactions, especially when substituent(s) lie on the cyclic carbonate rings. When these amines are used, it is preferred to use one or a combination of the known catalysts for this opening reaction, such as strongly basic amines (such as diazabicyclooctane, tetramethylguanidine), strongly basic quaternary ammonium compounds (such as alkyl(C16-C22)benzyltrimethyl ammonium hydroxide or carbonate and tetrabutylammonium hydroxide or carbonate), supranucleophilic catalysts (such as 4-pyrrolidinepyridine, poly(N,N-dialkylaminopyridine, dimethylaminopyridine), base anions whose conjugate acid has a pKa of about 11 or more (such as tert-butoxide).

While it is preferred not to use any solvent for the preparation reaction of the hydroxyalkyl carbamates, the latter may be used, for example, in order to improve the compatibility of a reagent or a catalyst such as the reaction mixture is homogeneous throughout the reaction.

In the hydroxyalkyl carbamates of formula (I), (II), (III), (IV) and in the cyclic carbonates of formula (XIII) used in the process according to the invention k Is preferably at most 3, most preferably k is 2.

In the hydroxyalkyl carbamates of formula (V), (VI) and (VII) and in the cyclic carbonates of formula (XIV), (XV) and (XVI) used in the process according to the invention n, m, p, q, r, s, v and w are, independently, preferably 0 or 1.

In the hydroxyalkyl carbamates of formula (V), (VI) and (VII) and in the cyclic carbonates of formula (XIV), (XV) and (XVI) used in the process according to the invention n+m, p+q, r+s, v+w, are preferably 1.

In the hydroxyalkyl carbamates of formula (I), (II), (III), (IV), (V), (VI) and (VII) and in the cyclic carbonates of formula (XIII), (XIV), (XV) and (XVI) used in the process according to the invention each $R^1$ and each $R^2$ is, independently, preferably chosen from the group of hydrogen; alkyl comprising from 1 to 6 carbon atoms, optionally substituted by hydroxy or halogen; and alkenyl comprising from 1 to 6 carbon atoms; both optionally containing from 1 to 3 ether bridges.

In the hydroxyalkyl carbamates of formula (I), (II), (III), (V), (V), (VI) and (VII) and in the cyclic carbonates of formula (XIII), (XIV), (XV) and (XVI) used in the process according to the invention, preferably, all but one of the $R^1$ substituents are hydrogen. In these preferred hydroxyalkyl carbamates, all but one of the $R^2$ substituents are preferably hydrogen. Most preferably, in these hydroxyalkyl carbamates, all $R^2$ substituents are hydrogen.

Particularly preferred hydroxyalkyl carbamates of formula (I), (II), (III) and (IV) and particularly preferred cyclic carbonates of formula (XIII) are those wherein one of the $R^1$ substituents is chosen from the group of hydrogen, methyl, ethyl, hydroxymethyl, chloromethyl, allyloxymethyl, and wherein the $R^2$ substituent present on the same carbon atom as this $R^1$ substituent is chosen from hydrogen and methyl, all other $R^1$ and all other $R^2$ substituents being hydrogen.

Particularly preferred hydroxyalkyl carbamates of formula (V), (VI) and (VII) and particularly preferred cyclic carbonates of formula (XIV), (XV) and (XVI) are those wherein each $R^1$ and each $R^2$ is hydrogen.

In the hydroxyalkyl carbamates of formula (V), (VI) and (VII) and in the cyclic carbonates of formula (XIV), (XV) and (XVI) used in the process according to the invention each $R^{20}$ is preferably hydrogen.

In the hydroxyalkyl carbamates of formula (I) (V), (VI) and (VII) and in the amines of, formula (IX) used in the process according to the invention $R^3$ is preferably an alkyl, optionally substituted by hydroxy, tertiary amine and/or aryl, and optionally containing from 1 to 20 ether bridges. Most preferably, $R^3$ is chosen from the group of alkyl comprising up to 10 carbon atoms, optionally substituted by one hydroxy or tertiary amine and/or optionally containing one or two ether bridges. Non-limiting examples are $R^3$ substituents chosen from the group of n-propyl, isopropyl, n-butyl, isobutyl, sec-butyl, tert-butyl, n-hexyl, n-octyl, 2-ethylhexyl, isononyl, cyclopentyl, cyclohexyl, 2-methylcyclohexyl, N,N-(di-tert-butyl)ethyl, benzyl, 2-(2-hydroxyethoxy)ethyl, 5-hydroxypentyl, 2-hydroxyethyl, 2-hydroxypropyl, 3-hydroxypropyl, 3-(diethylamino)propyl, 2,(diethylamino)ethyl, 1-methyl-4-(diethylamino)butyl, 2-((di-tert-butyl)amino)ethyl, 3-(dimethylamino)propyl, 2-methoxyethyl, 2-ethoxyethyl, 3-methoxypropyl, 2-methoxyisopropyl, 3-ethoxypropyl, 3-isopropoxypropyl, 3-(2-methoxyethoxy)propyl, 3-(2-ethylhexyloxy)propyl, $CH_3O(CH_2CH_2O)_6$—$(CH_2CHR$—$O)_{10}$—$CH_2$—$CH(CH_3)$—
wherein R is H or $CH_3$ in a proportion of 1:9, ethyl, methyl, 1,2-dimethylpropyl.

In the hydroxyalkyl carbamates of formula (I), (V), (VI) nd (VII) and in the amines of formula (IX) used in the process according to the invention $R^4$ is preferably chosen from the group of hydrogen and alkyl, optionally substituted by hydroxy, tertiary amine or aryl, and optionally containing from 1 to 8 ether bridges. Most preferably, $R^4$ is chosen from the group of hydrogen and alkyl comprising up to 10 carbon atoms, optionally substituted by one hydroxy or tertiary amine and/or optionally containing one or two ether bridges. Non-limiting examples are $R^4$ substituents chosen from the group of hydrogen, ethyl, n-propyl, isopropyl, n-hexyl, methyl, tert-butyl, n-butyl, isobutyl, n-octyl, 2-ethylhexyl, 1,2-dimethylpropyl, cyclohexyl, 2-hydroxyethyl, 2-hydroxyisopropyl, 3-hydroxypropyl, 2-methoxyethyl, 3-(dimethylamino)propyl.

In the hydroxyalkyl carbamates of formula (I), (V), (VI) and NV) and in the amines of formula (X) used in the process according to the invention $R^4$ is more preferably hydrogen and $R^3$ is as defined here above, more specifically $R^3$ is an alkyl comprising at least 3 carbon atoms and substitued by at least one hydroxy and optionally containing one or two ether bridges. Particularly preferred $R^4$ is hydrogen and $R^3$ is 2-(2-hydroxyethoxy)ethyl.

In the hydroxyalkyl carbamates of formula (II), (III), (IV) and in the amines of formula (X) (XI) and (XII) used in the process according to the invention $R^5$, $R^6$, $R^{12}$, $R^{13}$, $R^{14}$, $R^{15}$ and $R^{16}$ are preferably, independently, chosen from the group of hydrogen and alkyl comprising up to 10 carbon atoms, most preferably up to 6 carbon atoms.

In the hydroxyalkyl carbamates of formula (I), (II), (IV), (V), (VI) and (VII) and in the amines of formula (IX), (X), (XI) and (XII) used in the process according to the invention $R^3$ and $R^4$, $R^5$ and $R^6$, $R^{12}$ and/or $R^{13}$ and/or $R^{14}$, $R^{15}$ and $R^{16}$, respectively, may be linked together in order to form a ring. In this case, these substituents are preferably linked so that they form an alkylene chain comprising from 2 to 7 carbon atoms, and optionally containing 1 or 2 ether bridges. In case of $R^3$ and $R^4$, this alkylene chain is preferably such that a 5 to 7-membered ring is formed, for example a pyrolidine ring, a piperidine ring or a morpholine ring, which may further be substituted by alkyl groups. In case of $R^5$ and $R^6$, this alkylene chain is preferably such that a 5 to 7-membered ring is formed, for example piperazine, which may further be substituted by alkyl groups.

In the hydroxyalkyl carbamates of formula (II) and in the amines of formula (X) used in the process according to the invention $R^7$ is preferably chosen from the group of alkylene and aralkylene chains, containing up to 20 carbon atoms and which may contain from 1 to 8 ether bridges and/or from 1 to 3 tertiary amine bridges. Most preferably, $R^7$ is chosen from the group of ethylene, 1,2-propylene, trimethylene, hexamethylene, 2,2-dimethylpropylene, 1-methyltrimethylene, 1,2,3-trimethyltetramethylene, 2-methyl-pentamethylene, 2,2,4-(or 2,4,4-)trimethylhexamethylene, metaxylylene, 3,5,5-trimethylcyclohexyl-1-ene-3-methylene, bis(cyclohexyl-4-ene)methane, bis(4-methylcyclohexyl-3-ene) methane, cyclohexyl-1,3-ene, cyclohexyl-1,4-ene, 1,4-bis (propoxyl-3-ene)butane, N,N-bis(trimethylene) methylamine, 3,6-dioxaoctylene, 3,8-dioxadodecylene, 4,7,10-trioxatridecylene, poly(oxytetramethylene), poly (oxypropylene) with 2 to 15 1,2-propylene oxide units, poly(oxypropylene-co-oxyethylene) with 2 to 15 propylene oxide and 2 to 15 ethylene oxide units, 2,2-dimethylpropylene.

In the hydroxyalkyl carbamates of formula (III) and in the amines of formula (XI) used in the process according to the invention $R^8$, $R^9$, $R^{10}$ are preferably, independently, chosen from the group of alkylene, optionally containing from 1 to 8 ether bridges. Most preferably $R^8$, $R^9$, $R^{10}$ are chosen from alkylene comprising up to 15 carbon atoms and containing up to 5 ether bridges.

In the hydroxyalkyl carbamates of formula (IV) and in the amines of formula (XI) used in the process according to the invention $R^{17}$ and $R^{18}$ are preferably, independently, chosen from the group of alkylene. Most preferably $R^{17}$ and $R^{18}$ are chosen from alkylene comprising up to 6 carbon atoms.

In the hydroxyalkyl carbamates of formula (III) and in the amines of formula (XI) used in the process according to the invention $R^{11}$ is preferably hydrogen or an alkyl containing from 1 to 4 carbon atoms.

In the hydroxyalkyl carbamates of formula (V) and in the cyclic carbonates of formula (XIV) used in the process according to the invention $R^{19}$ is preferably chosen from alkylene and aralkylene chains which may contain from 1 to 20 ether bridges. Prefered are alkylene and aralkylene chains comprising at least 2 ether bridges.

In the hydroxyalkyl carbamates of formula (VI) and (VIN and in the cyclic carbonates of formula (XV) and (XVI) used in the process according to the invention $R^{21}$, $R^{22}$, $R^{23}$, $R^{25}$, $R^{26}$, $R^{27}$ and $R^{28}$, are preferably, independently, chosen from alkylene and aralkylene chains which may contain from 1 to 3 ether bridges.

In the hydroxyalkyl carbamates of formula (VI) and in the cyclic carbonates of formula (XV) used in the process according to the invention $R^{24}$ is preferably hydrogen or alkyl comprising form 1 to 4 carbon atoms.

Cyclic carbonates such as used in the process according to the invention are known in the art or can easily be prepared by known methods. Cyclic carbonates of formula (XIII) wherein k=2 and cyclic carbonates of formulas (XIV), (XV) and (XVI) wherein n+m, p+q, r+s or v+w are equal to 1 can easily be prepared by the reaction of the corresponding epoxides with carbon dioxide. Typical reaction conditions are described in Kihara, N., Hara, N., Endo, T., J. Org. Chem., 1993, 58, 6198., J. Org. Chem., 1993, 58, 6198-6202. Some of the catalysts described hereabove for the preparation of the hydroxyalkyl carbamates by opening of the cyclic carbonate with the amine, are also known as catalysts for the reaction between carbon dioxide and an epoxide group. Cyclic carbonates of formula (XII) wherein k=2 and cyclic carbonates of formulas (XIV), (XV) and (XVI) wherein n+m, p+q, r+s or v+w are equal to 1 can easily be prepared by the reaction of the corresponding epoxides with carbon dioxide. In this case, it is preferred to choose a catalyst active for both the formation of the cyclic carbonate group(s) and their opening by the amine.

Cyclic carbonates of formula (XIII) wherein k=3 can be prepared by transesterification of propane-1,3-diols with dialkyl carbonates such as described for example in Hu, B., Zhuo, R. X., Fan, C. L., Polym. Adv. Technol., 1998, 9, 145. Cyclic carbonates of formulas (XIV), (XV) and (XVI) wherein n+m, p+q, r+s or v+w are equal to 2 can be prepared by transesterification of polyols containing several propane-1,3-diols groups such as ditrimethylolpropane with dialkyl carbonates. They can also be obtained by reacting 6-membered cyclic carbonates containing one functional group such as OH group in 5-ethyl-5-hydroxymethyl-1,3-dioxan-2-one with coupling agents such as multifunctional chloroformates.

Cyclic carbonates of formula (XIII) wherein k>3 and cyclic carbonates of formulas (XIV), (XV) and (XVI) wherein n+m, p+q, r+s or v+w are >2 can be prepared according to the same transesterification reaction pathwasys as that leading to the lower-membered rings (Matsuo, J. et al., J. Polym. Sci. A: Polym. Chem., 1997, 35, 1375).

Cyclic carbonates of formula (XIII) which are particularly useful in the process according to the invention are 1,3-dioxolan-2-one (ethylene carbonate), 4-methyl-1,3-dioxolan-2-one(propylene carbonate), 4-ethyl-1,3-dioxolan-2-one(butylene carbonate), 4-hydroxymethyl-1,3-dioxolan-2-one (glycerine carbonate), 4-chloromethyl-1,3-dioxolan-2-one, 4-allyloxymethyl-1,3-dioxolan-2-one, 5,5-dimethyl-1,3-dioxan-2-one, (neopentylglycol carbonate).

Cyclic carbonates of formulas (XIV), (XV) and (XVI) which are particularly useful in the process according to the invention are those obtained from the reaction of carbon dioxide with polyepoxide compounds, such as the polyglycidyl ethers of aliphatic or aromatic polyols, such as, for example, 1,4-butanediol, neopentylglycol, cyclohexanedimethanol, diethyleneglycol, polyethyleneglycol, dipropyleneglycol, polypropyleneglycol, 2,2,4-trimethyl-1, 3-pentanediol, 1,6-hexanediol, trimethylolpropane, trimethylolethane, glycerol, 4,4'-isopropylidenediphenol, 1,1,1-tris(4-hydroxyphenyl)ethane, hydroquinone, 4,4'-bisphenol, 2,2'-bisphenol, 4,4'-dihydroxybenzophenone, 1,5-dihydroxynaphthalene, resorcinol. Preferred are the polyglycidyl ethers of aliphatic polyols, and most preferred the diglycidyl ether of polypropyleneglycol containing from 2 to 15 1,2-propylene oxide units.

Amines of formula (IX), (X) (XI) and (XII) are known in the art. Amines of formula (IX) which are particularly useful in the process according to the invention are n-propylamine, isopropylamine, n-butylamine, isobutylamine, sec-butylamine, tert-butylamine, 3-methylbutylamine, n-hexylamine, n-octylamine, 2-ethylhexylamine, isononylamine, cyclopentylamine, cyclohexylamine, 2-methylcyclohexylamine, N,N-(di-tert-butyl)ethyleneamine, benzylamine, 2-(2-aminoethoxy)ethanol, 5-aminopentanol, ethanolamine, 1-aminopropan-2-ol, 3-amino-1-propanol, 3-(diethylamino) propylamine, 2-(diethylamino)ethylamine, 1-methyl-4-(diethylamino)butylamine, 2,2-(di-tert-butylamino)ethylamine, 3-(dimethylamino)propylamine, 2-methoxyethylamine, 2-ethoxyethylamine, 3-methoxypropylamine, 1-methoxyisopropylamine, 3-ethoxypropylamine, 3-isopropoxypropylamine, 3-(2-methoxyethoxy) propylamine, 3-(2-ethylhexyloxy)propylamine, α-oxymethyl-ω-(2-propylamino)-poly(oxypropylene-co-oxyethylene) with an average number of 1,2-propylene oxide units of 9 and an average number of ethylene oxide units of 7, also known as Jeffamine® M-600 (manufactured by Hunstman), diethylamine, di-n-propylamine, diisopropylamine, di-n-hexylamine, N-methylbutylamine, N-ethylbutylamine, di-n-butylamine, diisobutylamine, di-n-octylamine, bis(2-ethylhexyl)amine, N-ethyl-1,2-dimethylpropylamine, dicyclohexylamine, cyclohexylmethylamine, cyclohexylethylamine, N-methylbenzylamine, 2-methylaminoethanol, 2-ethylaminoethanol, 2-butylaminoethanol, diethanolamine, diisopropanolamine, 3-(2hydroxyethyl)aminopropanol, bis(2-methoxyethyl) amine, bis(3-dimethylaminopropyl)amine, pyrolidine, piperidine, morpholine, 2,6-dimethylmorpholine.

Amines of formula (X) which are particularly useful in the process according to the invention are ethylenediamine, 1,2-propylenediamine, trimethylenediamine, hexamethylenediamine, 2,2-dimethylpropane-1',3-diamine, 1-methyl-1, 3-propanediamine, 1,2,3-trimethyl-1,4-butanediamine, 2-methyl-1,5 diaminopentane, 2,2,4-(or 2,4,4-)trimethylhexamethylene diamine, metaxylylenediamine, 1-amino-3-aminomethyl-3,5,5 trimethylcyclohexane (isophorone diamine), bis-(4-aminocyclohexyl)-methane, bis-(4-amino-3-methyl-cyclohexyl)-methane, 1,3-cyclohexanediamine, 1,4-cyclohexanediamine, 1,4-Bis(3-aminopropoxy)butane diamine, N,N-bis(3-aminopropyl)methylamine, triethyleneglycol diamine, 3,3'-(butane-1,4-diylbis(oxy))bispropaneamine, 4,7,10-trioxatridecan-1,13-diamine, α-amino-ω-(4-butylamino)-poly(oxytetramethylene), α-amino-ω-(2-propylamino)-poly(oxypropylene) with an average number of 1,2-propylene oxide units of 2.6, also known as Jeffamine® D-230 (manufactured by Hunstman), α-amino-ω-(2-propylamino)-poly(oxypropylene) with an average number of 1,2-propylene oxide units of 5.6, also known as Jeffamine® D-400 (manufactured by Hunstman), α-amino-ω-(2-propylamino)-poly(oxypropylene-co-oxyethylene) with an average number of 1,2 propylene oxide units of 2.5 and ethylene oxide units of 8.5, also known as Jeffamine® ED-600 (manufactured by Hunstman), N,N'-dimethyl-1,3- propanediamine, N,N'-di-tert-butyl-ethanediamine, N,N'-dimethylhexyl-1,6-diamine, piperazine, 2,5-dimethylpiperazine.

Amines of formula (XI) that are particularly useful in the process according to the invention is propoxylated trimethylopropane triamine with an average number of number of 1,2-propylene oxide units of 5.3, also known as Jeffamine®T-403 (manufactured by Hunstman).

Amines of formula (XII) that are particularly useful in the process according to the invention are N,N-dimethyldipropylenetriamine, bis(hexamethylene)triamine.

The process according to the invention permits to produce low color carbamoyloxy (meth)acrylates, having a color index of below 2 Gardner, as measured according to ASIM D 1544-68.

The process according to the invention permits to obtain carbamoyloxy (meth)acrylates of high purity, containing no or less toxic side products than the processes disclosed in the prior art, even without the use of extra purification procedures. The process according to the invention permits to obtain products containing no residual isocyanates and no hydroxyethyl (meth)acrylate. The process according to the invention also presents the advantage that cheap and safe raw materials can be used. The process involving nor toxic raw materials nor highly exothermic reactions leading to atmospheric pollution with toxic materials, standard industrial equipments and safety procedures can be used at larger scale.

The process according to the invention permits to obtain new carbamoyloxy (meth)acrylates not known in the prior art, most of which are not obtainable by the current commercial processes such as the isocyanate process.

The present invention also relates to new carbamoyloxy (meth)acrylates that can be obtained with the process according to the present invention. The invention also relates to carbamoyloxy acrylates of formula (XVII), (XVIII), (XIX), (XX), (XXI), (XXII), (XXIII), (XXIV), (XXV) and (XXVI)

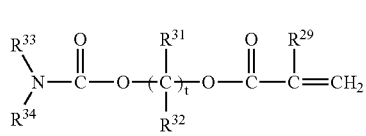
(XVII)

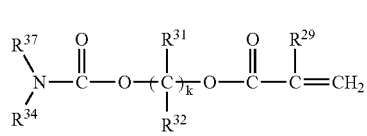
(XVIII)

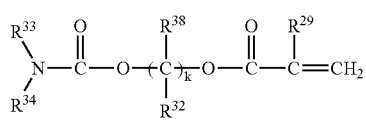
(XIX)

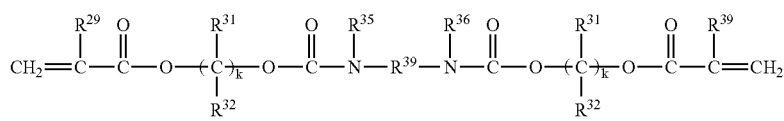
(XX)

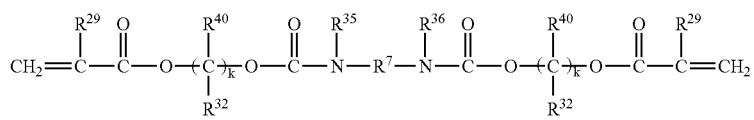
(XXI)

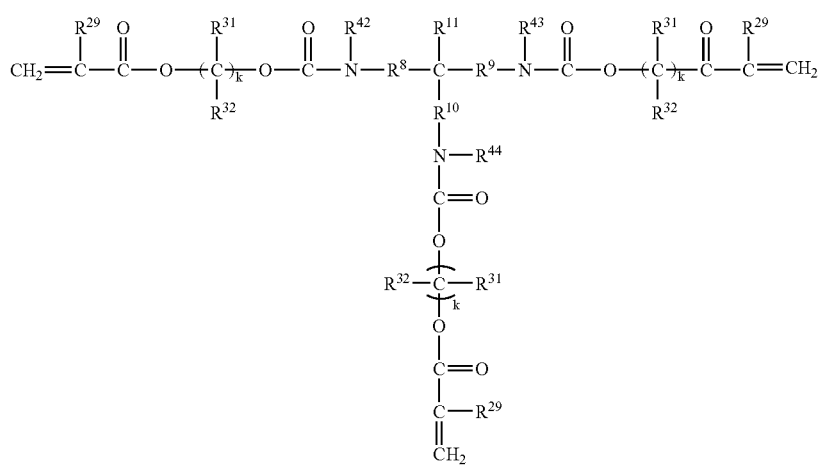
(XXII)

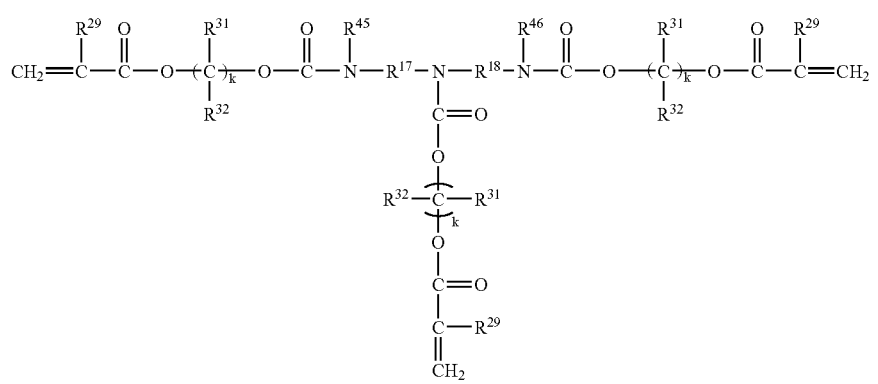
(XXIII)
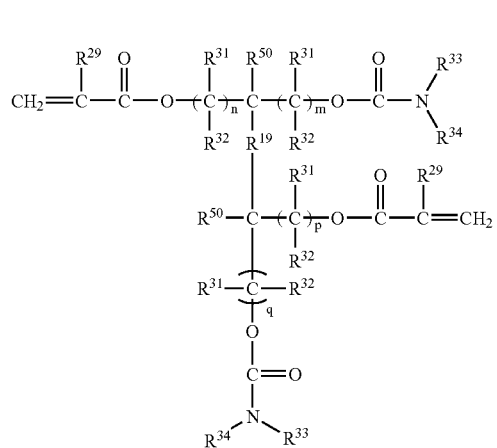
(XXIV)
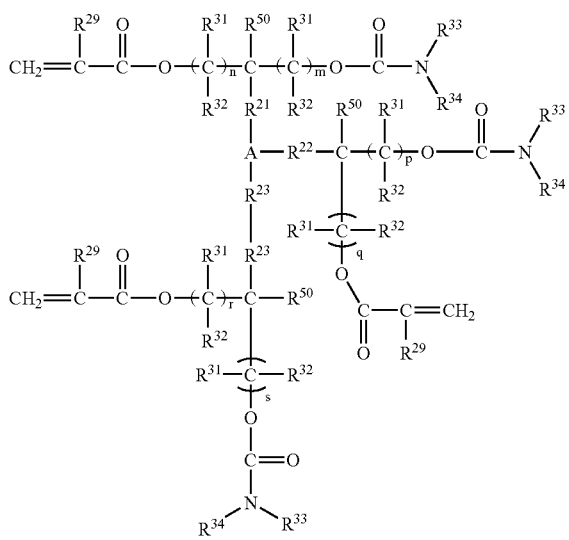
(XXV)
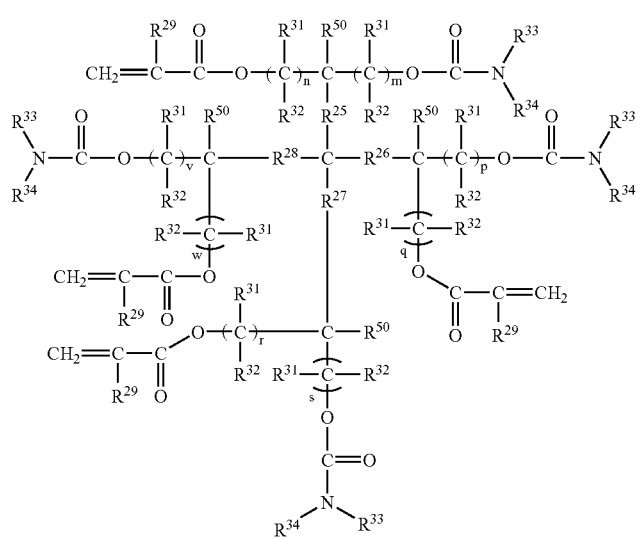
(XXVI)

wherein
k, n, m, p, q, r, s, v, w, A, $R^7$, $R^8$, $R^9$, $R^{10}$, $R^{17}$, $R^{18}$, $R^{11}$, $R^{19}$, $R^{21}$, $R^{22}$, $R^{23}$, $R^{24}$, $R^{25}$, $R^{26}$, $R^{27}$, $R^{28}$ and $R^{29}$ are as defined here above,
$t \geq 3$
$R^{37}$ is an alkyl substituted by a tertiary amine, and optionally containing from 1 to 20 ether bridges and/or from 1 to 3 tertiary amine bridges; or an alkyl containing from 1 to 20 ether bridges and/or from 1 to 3 tertiary amine bridges, optionally substituted by —O—CO—$CR^{29}$=$CH_2$, tertiary amine and/or aryl,;
each $R^{38}$, each $R^{40}$ is, independently, such as defined for $R^{31}$ with the proviso that at least one $R^{38}$ and at least one $R^{40}$ is chosen from the group of
  halogen
  —O—CO—$CR^{29}$=$CH_2$,
  alkyl substituted by —O—CO—$CR^{29}$=$CH_2$; halogen; aryl and/or aryl substituted by —O—CO—$CR^{29}$=$CH_2$, halogen or alkyl; and optionally containing from 1 to 8 ether bridges,
  alkyl containing from 1 to 8 ether bridges,
  alkenyl, optionally substituted by —O—CO—$CR^{29}$=$CH_2$; halogen; aryl and/or aryl substituted by —O—CO—$CR^{29}$=$CH_2$, halogen or alkyl; and optionally containing from 1 to 8 ether bridges,
  aryl, optionally substituted by —O—CO—$CR^{29}$=$CH_2$; halogen; alkyl; alkyl substituted by —O—CO—$CR^{29}$=$CH_2$, halogen and/or aryl; and/or alkyl containing from 1 to 8 ether bridges
$R^{39}$ is 2-methyl-1,5-pentamethylene, or $R^{39}$ is chosen from alkylene containing from 1 to 8 ether bridges and/or from 1 to 3 tertiary amine bridges; alkenylene, arylene and aralkylene chains each of which may contain from 1 to 8 ether bridges and/or from 1 to 3 tertiary amine bridges, or $R^{39}$ is chosen from alkylene when at least one of $R^{35}$ and $R^{36}$ is different from hydrogen,
each $R^{31}$, each $R^{32}$, each $R^{50}$ is, independently, chosen from the group of
  hydrogen,
  halogen
  —O—CO—$CR^{29}$=$CH_2$,
  alkyl, optionally substituted by —O—CO—$CR^{29}$=$CH_2$; halogen; aryl and/or aryl substituted by —O—CO—$CR^{29}$=$CH_2$, halogen or alkyl; and optionally containing from 1 to 8 ether bridges
  alkenyl, optionally substituted by —O—CO—$CR^{29}$=$CH_2$; halogen; aryl and/or aryl substituted by —O—CO—$CR^{29}$=$CH_2$, halogen or alkyl; and optionally containing from 1 to 8 ether bridges
  aryl, optionally substituted by —O—CO—$CR^{29}$=$CH_2$; halogen; alkyl; allyl substituted by —O—CO—$CR^{29}$=$CH_2$, halogen and/or aryl; and/or alkyl containing from 1 to 8 ether bridges
$R^{33}$ is an alkyl, optionally substituted by —O—CO—$CR^{29}$=$CH_2$, tertiary amine and/or aryl, and optionally containing from 1 to 20 ether bridges and/or from 1 to 3 tertiary amine bridges,
$R^{34}$, $R^{35}$, $R^{36}$, $R^{42}$, $R^{43}$, $R^{44}$, $R^{45}$ and $R^{46}$ are, independently, chosen from the group of
  hydrogen, and
  alkyl, optionally substituted by —O—CO—$CR^{29}$=$CH_2$, tertiary amine and/or aryl, and optionally containing from 1 to 8 ether bridges and/or from 1 to 3 tertiary amine bridges,
  with the proviso that, respectively, $R^{33}$ and $R^{34}$, $R^{35}$ and $R^{36}$, $R^{42}$ and/or $R^{43}$ and/or $R^{44}$, $R^{45}$ and $R^{46}$ may be linked together in order to form a ring.

In the carbamoyloxy (meth)acrylates of formula (XVII), t is preferably 3.

In the carbamoyloxy (meth)acrylates of formula (XVIII), $R^{37}$ is preferably chosen from the group of alkyl comprising up to 10 carbon atoms substituted by alkoxy comprising less than 6 carbon atoms or tertiary amine and/or optionally containing one or two ether bridges; and alkyl comprising up to 10 carbon atoms, containing one or two ether bridges and substituted by —O—CO—$CR^{29}$=$CH_2$. Non-limiting examples are $R^{37}$ substituents chosen from the group of N,N-(di-tert-butyl)ethyl, 3-(diethylamino)propyl, 2-(diethylamino)ethyl, 2-methyl-4-(diethylamino)butyl, 2,2-(di-tert-butylamino)ethyl, 3-(dimethylamino)propyl, 2-methoxyethyl, 2-ethoxyethyl, 3-methoxypropyl, 1-methoxyisopropyl, 3-ethoxypropyl, 3-isopropoxypropyl, 3-(2-methoxyethoxy)propyl, 3-(2-ethylhexyloxy)propyl, $CH_3O(CH_2CH_2O)_6$—$(CH_2CHR$—$O)_{10}$—$CH_2$—CH$(CH_3)$— wherein R is H or $CH_3$ in a proportion of 1:9, —$CH_2$—$CH_2$—O—$CH_2$—$CH_2$—O—CO—$CR^{29}$=$CH_2$.

In the carbamoyloxy (meth)acrylates of formula (XVIII), $R^{34}$ is preferably hydrogen and $R^{37}$ is as described here above, more specifically $R^{37}$ is alkyl comprising at least 3 carbon atoms, containing one or two ether bridges and substituted by —O—CO—$CR^{29}$=$CH_2$ In the carbamoyloxy (meth)acrylates of formula (XIX) and (XXI), each $R^{38}$, each $R^{40}$ is, preferably, independently, such as defined for $R^{31}$ with the proviso that at least one $R^{38}$ and at least one $R^{40}$ is chosen from the group of
  alkyl comprising from 1 to 6 carbon atoms and substituted by —O—CO—$CR^{29}$=$CH_2$ or halogen; and optionally containing from 1 to 3 ether bridges
  alkenyl comprising from 1 to 6 carbon atoms, and optionally containing from 1 to 3 ether bridges.

Most preferably, only one of $R^{38}$ and only one of $R^{40}$ is chosen from the group of alkyl comprising from 1 to 6 carbon atoms and substituted by —O—CO—$CR^{29}$=$CH_2$ or halogen; and optionally containing from 1 to 3 ether bridges; and alkenyl comprising from 1 to 6 carbon atoms, and optionally containing from 1 to 3 ether bridges; all other $R^{38}$ and $R^{40}$ groups being hydrogen. Particularly preferred carbamoyloxy (meth)acrylates of formula (XIX) are those wherein one of the $R^{38}$ substituents is chosen from the group of methyl substituted by —O—CO—$CR^{29}$=$CH_2$, chloromethyl and allyloxymethyl, all other $R^{38}$ and all $R^{32}$ being hydrogen.

In the carbamoyloxy (meth)acrylates of formula (XX), $R^{39}$ is preferably chosen from 2-methyl-1,5-pentamethylene, from alkylene containing up to 20 carbon atoms and containing from 1 to 8 ether bridges and/or from 1 to 3 tertiary amine bridges and from aralkylene chains containing up to 20 carbon atoms and which may contain from 1 to 8 ether bridges and/or from 1 to 3 tertiary amine bridges. Most preferred are poly(oxypropylene) with 2 to 15 1,2-propylene oxide units and poly(oxypropylene-co-oxyethylene) with 2 to 15 propylene oxide and 2 to 15 ethylene oxide units.

In the carbamoyloxy (meth)acrylates of formula (XVII), (XVIII), (XIX), (XX), (XXI), (XXII), (XXIII), (XXIV), (XXV) and (XXVI), each $R^{31}$ and each $R^{32}$ is, independently, preferably chosen from the group of hydrogen; alkyl comprising from 1 to 6 carbon atoms, optionally substituted by —O—CO—$CR^{29}$=$CH_2$ or halogen; and alkenyl comprising from 1 to 6 carbon atoms; both optionally containing from 1 to 3 ether bridges.

In the carbamoyloxy (meth)acrylates of formula (XVII), (XVIII), (XX), (XXI), (XXII), (XXIII), (XXIV), (XXV) and (XXVI), preferably, all but one of the $R^{31}$ substituents are hydrogen. In these preferred carbamoyloxy (meth)acrylates, all but one of the $R^{32}$ substituents are preferably hydrogen. Most preferably, in these carbamoyloxy (meth)acrylates, all $R^{32}$ substituents are hydrogen.

Particularly preferred carbamoyloxy (meth)acrylates of formula (XVII), (XVIII), (XX), (XXI), (XXII) and (XXIII) are those wherein one of the $R^{31}$ substituents is chosen from the group of hydrogen, methyl, ethyl, —$CH_2$—O—CO—$CR^{29}$=$CH_2$, chloromethyl, allyloxymethyl, and wherein the $R^{32}$ substituent present on the same carbon atom as this $R^{31}$ substituent is chosen from hydrogen and methyl, all other $R^{31}$ and all other $R^{32}$ substituents being hydrogen.

Particularly preferred carbamoyloxy (meth)acrylates of formula (XVIII) are those wherein all $R^{31}$ and all $R^{32}$ substituents are hydrogen.

Particularly preferred carbamoyloxy (meth)acrylates of formula (XXIV), (XXV) and (XXVI) are those wherein n+m, p+q, r+s and v+w are equal to 1, and more particularly those wherein each $R^{31}$, each $R^{32}$ and each $R^{50}$ is hydrogen.

In the carbamoyloxy (meth)acrylates of formula (XVII), (XIX), (XXIV), (XXV) and (XXVI), $R^{33}$ is preferably an alkyl, optionally substituted by —O—CO—$CR^{29}$=$CH_2$, tertiary amine and/or aryl, and optionally containing from 1 to 20 ether bridges. Most preferably, $R^{33}$ is chosen from the group of alkyl comprising up to 10 carbon atoms, optionally substituted by one —O—CO—$CR^{29}$=$CH_2$ group or tertiary amine and/or optionally containing one or two ether bridges. Non-limiting examples are $R^{33}$ substituents chosen from the group of n-propyl, isopropyl, n-butyl, isobutyl, sec-butyl, tert-butyl, n-hexyl, n-octyl, 2-ethylhexyl, isononyl, cyclopentyl, cyclohexyl, 2-methylcyclohexyl, N,N-(di-tert-butyl) ethyl, benzyl, —$CH_2$—$CH_2$—O—$CH_2$—$CH_2$—O—CO—$CR^{29}$=$CH_2$, —$(CH_2)_5$—O—CO—$CR^{29}$=$CH_2$, —$(CH_2)_2$—O—CO—$CR^{29}$=$CH_2$, —$CH_2$—$CH(CH_3)$—O—CO—$CR^{29}$=$CH_2$, —$(CH_2)_3$—O—CO—$CR^{29}$=$CH_2$, 3-(diethylamino)propyl, 2-(diethylamino)ethyl, 4-(diethylamino)pentyl 2-methyl-4-(diethylamino)butyl, 3-(tert-butylamino) ethyl 2,2-di(tert-butyl)ethyl, 3-(dimethylamino)propyl, 2-methoxyethyl, 2-ethoxyethyl, 3-methoxypropyl, 1-methoxyisopropyl, 3-ethoxypropyl, 3-isopropoxypropyl, 3-(2-methylethoxypropyl 3-(2-methoxyethoxypropyl, 3-(2-ethylhexyloxy)propyl, $CH_3O(CH_2CH_2O)_6$—$(CH_2CHR$—O$)_{10}$—$CH_2$—$CH(CH_3)$— wherein R is H or $CH_3$ in a proportion of 1:9, ethyl, methyl, 1,2-dimethylpropylamine.

In the carbamoyloxy (meth)acrylates of formula (XVII), (XVIII), (XIX), (XXIV), (XXV) and (XXVI), $R^{34}$ is preferably chosen from the group of hydrogen and alkyl, optionally substituted by —O—CO—$CR^{29}$=$CH_2$, tertiary amine and/or aryl, and optionally containing from 1 to 8 ether bridges. Most preferably, $R^{34}$ is chosen from the group of hydrogen and alkyl comprising up to 10 carbon atoms, optionally substituted by one —O—CO—$CR^{29}$=$CH_2$ group or tertiary amine and/or optionally containing one or two ether bridges. Non-limiting examples are $R^{34}$ substituents chosen from the group of hydrogen, ethyl, n-propyl, isopropyl, n-hexyl, methyl, tert-butyl, n-butyl, isobutyl, n-octyl, 2-ethylhexyl, 1,2-dimethylpropyl, cyclohexylamine, —$(CH_2)_2$—O—CO—$CR^{29}$=$CH_2$, —$CH_2$—CH$(CH_3)$—O—CO—$CR^{29}$=$CH_2$, —$(CH_2)_3$—O—CO—$CR^{29}$=$CH_2$, 2-methoxyethyl, 3-(dimethylamino)propyl.

In the carbamoyloxy (meth)acrylates of formula (XX), (XXI), (XXII) and (XXIII), $R^{35}$, $R^{36}$, $R^{42}$, $R^{43}$, $R^{44}$, $R^{45}$ and $R^{46}$ are preferably, independently, chosen from the group of hydrogen and alkyl comprising up to 10 carbon atoms, most preferably up to 6 carbon atoms.

In the carbamoyloxy (meth)acrylates of formula (XVII), (XVIII), (XIX), (XX), (XXI), (XXII) (XXIII), (XXIV), (XXV) and (XXVI), $R^{33}$ and $R^{34}$, $R^{35}$ and $R^{36}$, $R^{42}$ and/or $R^{43}$ and/or $R^{44}$, $R^{45}$ and $R^{46}$, respectively, may be linked together in order to form a ring. In this case, these substituents are preferably linked so that they form an alkylene chain comprising from 2 to 7 carbon atoms, and optionally containing 1 or 2 ether bridges. In case of $R^{33}$ and $R^{34}$, this alkylene chain is preferably such that a 5 to 7-membered ring is formed, for example a pyrolidine ring, a piperidine ring or a morpholine ring, which may further be substituted by alkyl groups. In case of $R^{35}$ and $R^{36}$, this alkylene chain is preferably such that a 5 to 7-membered ring is formed, for example piperazine, which may further be substituted by alkyl groups.

Carbamoyl (meth)acrylates of formula (XVII), (XVIII), (XIX), (XX), (XXI), (XXII), (XXIII), (XXIV), (XXV) and (XXVI) wherein $R^{34}$, at least one of $R^{35}$ and $R^{36}$, at least one of $R^{42}$, $R^{43}$ and $R^{44}$ and at least one of $R^{45}$ and $R^{46}$ are different from hydrogen are another aspect of the invention.

The carbamoyloxy (meth)acrylates according to the invention are useful in the manufacture of radiation curable compositions. The carbamoyloxy (meth)acrylates according to the invention can be used in any known radiation-curable coating compositions (e.g. for wood, glass fibers, etc.), printing inks, photoresists, adhesives, decoration for paper, glass and packages, gravure images and other applications containing (meth)acrylates with carbamate residues.

The carbamoyloxy (meth)acrylates according to the invention having a molecular weight lower than 400 are very useful as reactive diluents in radiation curable compositions. The carbamoyloxy (meth)acrylates according to the invention having a molecular weight of at least 400, preferably higher than 400 and most preferably not exceeding 3000, can be used as oligomers in radiation curable compositions.

The carbamoyloxy (meth)acrylates of formula (XXIV), (XXV) and (XVI) have in general a much lower viscosity as compared to existing carbamoyloxy (meth)acrylates having similar molecular weights and same acrylate functionality.

The new low viscous carbamoyloxy (meth)acrylates allow reducing significantly the amount of reactive diluents needed to make the radiation-curable formulations. This allows maximizing properties specifically brought by (meth)acrylates with carbamate residues (adhesion, abrasion resistance . . . ) and makes possible the use of carbamoyloxy (meth)acrylates to applications where the viscosity of the formulation should be very low, such as spray coatings. Besides lowering the overall irritancy and smell of the formulation, reducing the amount of reactive diluents also allows reducing the well-known detrimental effect(s) the latter may have on specific coatings and inks properties. For example, reducing the amount of reactive diluents in UV parquet topcoats formulations is indeed well-known to improve significantly their abrasion resistance. In radiation-curable flexographic inks and varnishes used in food packaging, reducing the amount of reactive diluents are known to reduce significantly migration and off-odor problems.

EXAMPLES

Example 1

Preparation of n-butyl acryloyloxy ethyl carbamate

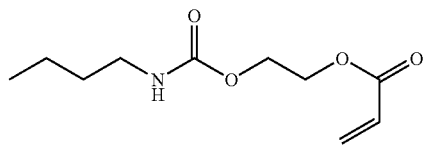

1/Preparation of 2-hydroxyethyl butyl carbamate from butyl amine and ethylene carbonate 253.4 g (3.47 moles) of butylamine was charged in a double-wall glass reactor with a capacity of 21 sparged with nitrogen. The reactor was fitted with an agitator, a thermometer, a gas inlet tube, a double-wall glass addition funnel, a connection to vacuum and an vacuum-Jacketed distillation column. A liquid semi-automatic splitter using a solenoid-activated PTFE valve and timer was used to control the reflux and takeoff from the distillation column into a cooled double-walled receiving flask. The splitter and a double-walled condenser connected to a cooling unit (−5° C.) were fitted on top of the distillation column.

277.4 g (3.15 moles, equivalent ratio amine to cyclic carbonate=1.1) of pre-melted ethylene carbonate (EC, sold by Hunstman) was slowly added from the funnel at a temperature of 45° C. Addition rate was chosen such as that the temperature in the reactor did not exceed 60° C.

Titration of the amine indicated that the reaction was complete at the end of the alimentation. The amine excess was stripped at 60° C. for 2 hours. A GC characterization of the hydroxycarbamate indicated that a >98% w/w pure product is obtained. 300 ppm free ethylene glycol was detected, but may be accounted entirely for the ethylene glycol coming from the starting ethylene carbonate (600 ppm).

2/Acrylation of 2-hydroxyethyl butyl carbamate by transesterification

Transesterification of 2-hydroxyethyl butyl carbamate was carried out adding 1220 g (14.2 moles, equivalent ratio alkyl acrylate to hydroxyalkyl carbamate=4.5) methyl acrylate, 300 ppm on end product of 2,6-di-tert-butyl-4-methylphenol (BHT) and 300 ppm on end product phenotiazine (PTZ). At this stage, air was injected throughout the reaction mixture.

Before adding the catalyst, about 10% of extra methyl acrylate (120 g) was added in the reactor and this extra amount was distilled over at 73° C. in order to dry the reaction mixture (b.p. water/methylacrylate azeotrope=72° C.). At this stage, the water content dropped below 100 ppm as measured by coulometry.

After addition of a mixture containing 80/20 w/w isopropyl titanate/n-butyl titanate (Tyzor TPT-20B manufactured by Dupont) (24 g, weight ratio of catalyst to the generated carbamoyloxy (meth)acrylate=0.035)), the reaction mixture was maintained at 65° C. by applying a slight vacuum (600 mmHg) and the methanol generated was taken off overhead as a methanol/methyl acrylate azeotrope, such a removal being followed by a temperature sensor located at the column's head. The azeotrope was removed as soon as the temperature at the top of the column dropped down to 50° C. Refractive index measurements of the distillate showed that at this temperature the azeotrope composition is near to theoretical (54% w/w methanol). The reaction was continued until a measure of the refractive index indicated that no more methanol was present in the distillate. Reaction time was 10.5 hours.

3/Work-up

After complete reaction, the catalyst was hydrolyzed by adding water (3 g per g catalyst). Stirring vigorously the mixture at 70° C. for 1.5 hour was found sufficient for complete hydrolysis of the catalyst, as evidenced by the disappearance of the yellowish color of the organic phase.

Diatomeceaous earth was added to the reaction mixture to aid the filtration of the white precipitate thus obtained. Vacuum filtration occurred utilizing a side-arm filtering flask and a 3-liter filter funnel wherein an diatomeceous earth bed had been deposited on a paper filter. Less than 30 minutes was needed to obtain a clear mixture.

The methyl acrylate excess was removed by concentration/stripping under vacuum (100 mmHg) at 75° C. for 2 hours. Air was injected during concentration/stripping to prevent polymerization. The final product was almost colorless and contained 6 ppm residual titanium as measured by atomic absorption spectrometry.

Comparative Example 2R

Preparation of n-butyl acryloyloxy ethyl carbamate by the Direct Esterification Method 1/Acrylation of 2-hydroxyethyl butyl carbamate by Direct Esterification Direct esterification of 2-hydroxyethyl butyl carbamate prepared such as described in Example 1 (1/) was carried out adding to a double-wall glass reactor (1.51) fitted with an agitator, a thermometer, a gas inlet tube, a connection to vacuum and an azeotropic distillation column having a Dean-Stark separator at its overhead, 332 g (2 moles) 2-hydroxyethyl butyl carbamate, 202 g (2.8 moles) acrylic acid, 350 g toluene (37% by weight of the reacting mixture), 500 ppm on end product methyl ether hydroquinone (MeHQ), and 0.1% on end product $H_3PO_2$. PTSA (p-toluenesulfonic acid, 70 g) was added to reach an end concentration of 18% mol on starting hydroxyalkyl carbamate. An air sparge was injected to prevent gelation.

Pressure was reduced in the reaction vessel to about 350 mmHg in order to allow reflux of a toluene/water azeotrope. The mixture was heated to 70° C. and stirred until no more water was distilled over. After 6 hours, 33 g (77% of the theoretical value) of esterification water was collected in the Dean Stark.

2/Work-up

When no more water was distilled over, the mixture was cooled to 60° C. and neutralized by the addition of 140 g of a 50% solution of NaOH in water. This mixture was washed three times with 20% by weight of the reacting mixture with water containing 20% NaCl, dried via azeotropic distillation with air sparging to remove all the water and finally filtered. The toluene was distilled and stripped under vacuum (30 mmHg) to remove all traces of toluene. Air was sparged to prevent polymerization/gelation.

Comparative Example 3R

Preparation of n-butyl acryloyloxy ethyl carbamate by Transesterification Using a Lower Amount of Methylacrylate Example 1 was repeated, except that the transesterification of 2-hydroxyethyl butyl carbamate was carried out by adding 809.3 g (9.4 moles, equivalent ratio alkylacrylate to hydroxyalkyl carbamate=3) methyl acrylate.

The reaction was continued until a measure of the refractive indicated that no more methanol was present in the distillate. Reaction time was 14.5 hours. The table here below gives the results (GC compositions) obtained in the different examples, together with the analysis of Genomer 1122 (commercial product supplied by Rahn, as which was prepared by the isocyanate method).

| Product | Purity (% w/w) | BuNCO* (% w/w) | HEA[x] (% w/w) | MA[+] (% w/w) | Color (Apha) |
|---|---|---|---|---|---|
| Example 1 | 96.5 | n.d. | n.d. | n.d. | 36 |
| Comparative Example 2R | 75 | n.d. | 0.8 | n.d. | 25 |
| Genomer® 1122 | 94.4 | 0.25 | 0.2 | n.d. | 15 |
| Comparative example 3R | 77.2 | n.d. | 0.12 | n.d. | 41 |

*butyl isocyanate.
[x]hydroxyethyl acrylate.
[+]methyl acrylate.

These results clearly show that the process according to the invention gives, at the same time, very good purity, no or very low amount of toxic by-products and very low coloration.

Example 4

Preparation of n-butyl acryloyloxy ethyl carbamate Using an Organotin Catalyst

Example 1 was repeated, except that the organotitanate catalyst Tyzor TPT-20B was replaced by n-butyl tin tris(2-ethylhexanoate). The catalyst concentration was chosen such as Sn content was the same as Ti content in Example 1.

The same results as in Example 1 were obtained except that the transesterification reaction was complete only after 16 h, hence compared to the organotitanate catalyst, the reaction rate was lower.

Example 5

Preparation of 2-Propenoic acid, 3,8-dioxo-7-oxa-6-azaethane-1,10-diyl ester

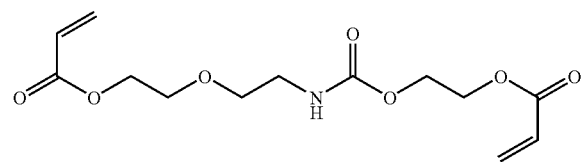

The starting hydroxyalkyl carbamate was obtained by adding 139.2 g (1.58 moles) EC on 166.1 g (1.58 moles) 2-(2-aminoethoxyethanol) (equivalent ratio amine to cyclic carbonate=1) in same conditions as in Example 1, except that an aromatic phosphite was also added (trisnonylphenylphosphite, 2000 ppm based on the quantity of hydroxyalkyl carbamate formed) in order to avoid oxidation of the amine. Titration of the amine indicated that the reaction was completed after maintaining the reaction mixture 3 hours at 60° C. after at the end of the alimentation. A GC characterization of the hydroxyalkyl carbamate indicated that a >97% w/w pure product was obtained.

The hydroxyalkyl carbamate was then acrylated using the same conditions as in Example 1 using 1220 g (14.2 moles, equivalent ratio alkyl acrylate to hydroxyalkyl carbamate=4.5) methyl acrylate, 300 ppm on end product of BHT, 300 ppm on end product of PTZ and 17.1 g of Tyzor TPT-20B (weight ratio of catalyst to the generated carbamoyloxy (meth)acrylate=0.036). After a same work-up procedure as in Example 1, a low colored product (1.5 Gardner) with a GC purity of 95.3% w/w and a Höppler viscosity at 25° C. of 89 mPa·s was obtained.

This product was very suitable as diluent in radiation curable compositions.

Example 6

Preparation of 2-Propenoic acid, 7,7,9 (or 7,9,9)-trimethyl-4,13-dioxo-3,14-dioxa-5,12-diazahexadecane-1,16-diyl ester

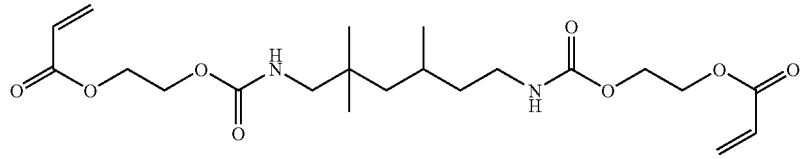

The starting hydroxyalkyl carbamate was obtained by slowly adding 228.8 g (2.6 moles) EC on 205.8 g (1.3 moles) 2,2,4-(or 2,4,4-)trimethylhexamethylene diamine (equivalent ratio amine to cyclic carbonate=1) such as the maximum temperature was 70° C. Titration of the amine showed that the reaction was done after an additional 4 hours at 70° C. $^1$H NMR indicated a conversion rate in expected product of 98% mol.

The hydroxyalkyl carbamate was then acrylated using the same conditions as in Example 1 using 1005 g (11.7 moles, equivalent ratio alkyl acrylate to hydroxyalkyl carbamate=4.5) methyl acrylate, 300 ppm on end product BHT, 300 ppm on end product of PIZ and 33.5 g of Tyzor TPT-20B (weight ratio of catalyst to the generated carbamoyloxy (meth)acrylate=0.042). Reaction time was 11.5 hours. After a same work-up procedure as in Example 1, a low colored product (1.2 Gardner) with 96% of the OH groups from the starting hydroxyalkylcarbamate being acrylated according $^1$H NMR, was obtained.

Example 7

Preparation of 2-Propenoic acid, 1,7,14 (or 1,7,15 or 2,7,14)-trimethyl-4,12-dioxo-3,13-dioxa-5,11-diazapentadecane-1,15-diyl ester

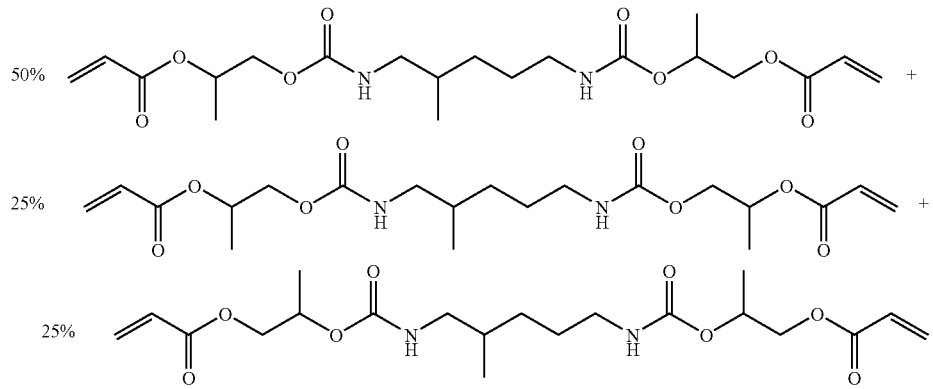

The starting hydroxyalkyl carbamate, obtained by reacting 2 moles of propylene carbonate with 1 mole of 2-methyl-1,5 diaminopentane, is commercially-available from King Industries Ltd. (K-flex UD-320-100).

Acrylation of K-flex UD-320-100 by transesterification was performed using same equipment as in Example 1. The reaction mixture containing 288.6 g K-flex UD-320-100 (0.85 moles), 1301 g (13 moles, equivalent ratio alkyl acrylate to hydroxyalkyl carbamate=7.6) ethyl acrylate, 1000 ppm on end product of BHT and 300 ppm on end product of PTZ was first dried by azeotropic distillation, as in Example 1. After adding 25.5 g Tyzor TPT-20B (weight ratio of catalyst to the generated carbamoyloxy (meth) acrylate=0.07), the reaction mixture was maintained at 102-103° C. and the ethanol generated was taken off overhead as a ethanol/ethyl acrylate azeotrope. The reaction was continued until a measure of the refractive index indicated that no more ethanol was present in the distillate. Reaction time was 10 hours. After a same work-up procedure as in Example 1, a low colored product (1.9 Gardner) with 92% of the OH groups from the starting hydroxyalkylcarbamate being acrylated according $^1$H NMR, was obtained.

In another experiment, glycerol was used instead of water to precipitate the catalyst. In that case, filtration time was decreased by a factor 5.

Example 8

Preparation of 2-Propenoic acid, 2-[[3-[(1-oxo-2-propenyl)oxy]-2-[[(butylamino)carbonyl]oxy]propoxy]butoxy]-1-[[[(butylamino)carbonyl]oxy]methyl] ethyl ester and isomers

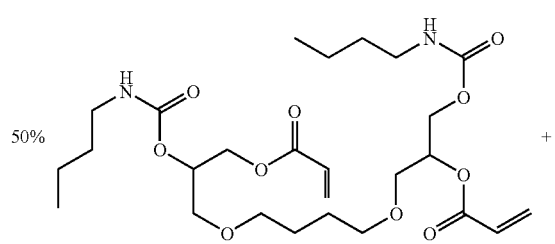

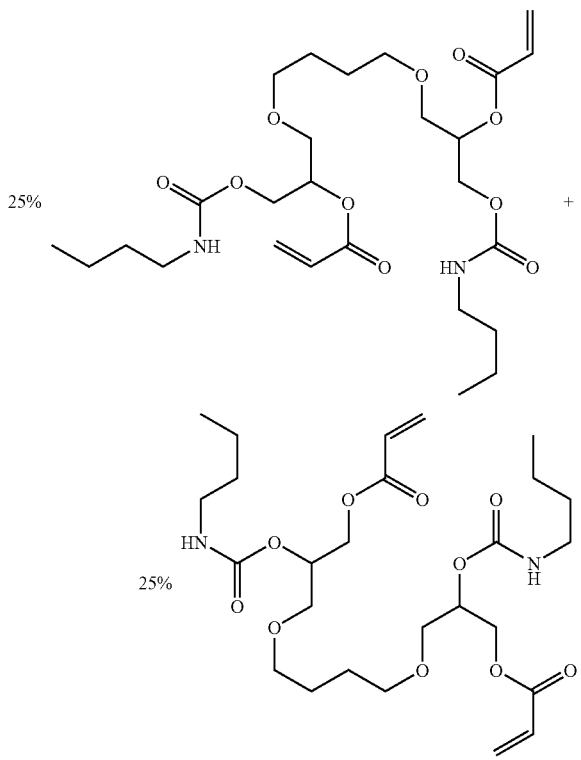

1/Preparation of 1,3-Dioxolan-2-one, 4,4'-[1,4-butanediyl-bis(oxymethylene)]bis)-

The latter was prepared from Oxirane, 2,2'-[1,4-butanediylbis(oxymethylene)]bis)-, commercially-available from EMS-Chemie as Grilonit RV 1806, and $CO_2$ with the procedure described in Kihara, N., Hara, N., Endo, T., J. Org. Chem., 1993, 58, 6198. $^1$H NMR indicated complete transformation of the oxirane into cyclic carbonate groups. Potentiometric titration of the cyclocarbonate groups of the final product lead to a cyclic carbonate equivalent weight of 163.5 g/eq (theory: 145 g/eq).

2/Preparation of [2-[[3-hydroxy-2-[[(butylamino)carbonyl]oxy]propoxy]butoxy]-1-[[[(butylamino)carbonyl]oxy]methyl]ethyl]hydroxy and isomers 282.9 g 1,3-Dioxolan-2-one, 4,4'-[1,4-butanediylbis(oxymethylene)]bis) prepared in 1/and 138.5 g (1.9 moles, equivalent ratio amine to cyclic carbonate=1.1) butylamine was charged in the same reactor as described in Example 1. The mixture was slowly heated to 70° C. Titration of the amine indicated that the reaction was complete after 3 h at 70° C. The amine excess was stripped at 70° C. for 4.5 hours.

A FTIR spectrum of the stripped product indicated the almost complete disappearance of the absorption band at 1797 cm$^{-1}$, characteristic of the carbonyl functions of the cyclic carbonate groups. $^1$H NMR indicated that the expected reaction occurred quantitatively (97% mol) to give a statistical mixture of the expected isomers.

3/Acrylation of [2-[[3-hydroxy-2-[[(butylamino)carbonyl]oxy]propoxy]butoxy]-1-[[[(butylamino)carbonyl]oxy]methyl] ethyl]hydroxy and isomers by transesterification Acrylation was then performed adding to the hydroxyalkyl carbamate prepared in 2/, 1251.3 g (12.5 moles, equivalent ratio alkyl acrylate to hydroxyalkyl carbamate=7.2) ethyl acrylate, 1000 ppm on end product of BHT and 300 ppm on end product of PTZ was first dried by azeotropic distillation, as in Example 1. After adding 23.6 g Tyzor TPT-20B (weight ratio of catalyst to the generated carbamoyloxy (meth)acrylate=0.05), the reaction mixture was maintained at 102-103° C. by injecting air and the ethanol generated was taken off overhead as a ethanol/ethyl acrylate azeotrope. The reaction was continued until a measure of the refractive index indicated that no more ethanol was present in the distillate. Reaction time was 12 hours. After a same work-up procedure as in Example 1, a low colored product (1.7 Gardner) with 95% of the OH groups from the starting hydroxyalkylcarbamate being acrylated according $^1$H NMR, was obtained.

Example 9

Preparation of α-[3-[(1-oxo-2-propenyl)oxy]-2-[[(butylamino)carbonyl]oxy]propoxy]-ω-[3-[[(butylamino)carbonyl]oxy]-2-[(1-oxo-2-propenyl)oxy]propyl]-poly[oxy(methyl-1,2-ethanediyl)] and isomers with an average number of oxy(methyl-1,2-ethanediyl) units between 9 and 10

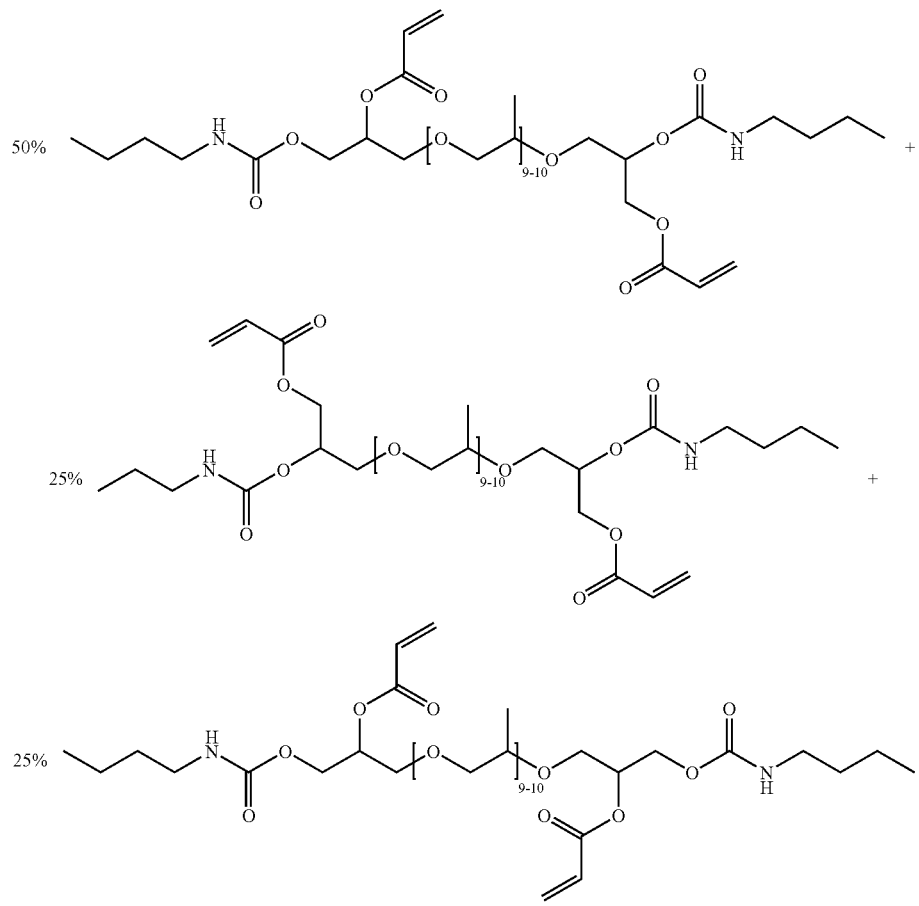

1/Preparation of α-[(2-oxo-1,3-dioxolan-4-yl)methoxy]-ω-[(2-oxo-1,3-dioxolan-4-yl)methyl]-poly[oxy(methyl-1,2-ethanediyl)] with an average number of oxy(methyl-1,2-ethanediyl) units between 9 and 10.

The latter was prepared from α-[oxiranylmethoxy]-ω-[oxiranylmethyl]-poly[oxy(methyl-1,2-ethanedlyl)] with an average number of oxy(methyl-1,2-ethanediyl) units between 9 and 10 (epoxide equivalent weight: 320 g/eq), commercially-available from Dow as D.E.R. 732P, and $CO_2$ with the procedure described in Kihara, N., Hara, N., Endo, T., J. Org. Chem., 1993, 58, 6198. $^1$H NMR indicated complete transformation of the oxirane into cyclic carbonate groups. Potentiometric titration of the cyclocarbonate groups of the final product lead to a cyclic carbonate equivalent weight of 382 g/eq (theory: 365 g/eq).

2/Preparation of α-[3-hydroxy-2-[[(butylamino)carbonyl]oxy]propoxy]-ω-[3-[[(butylamino)carbonyl]oxy]-2-[hydroxypropyl]-poly[oxy(methyl-1,2-ethanediyl)] and isomers with an average number of oxy(methyl-1,2-ethanediyl) units between 9 and 10.

500 g of the α-[(2-oxo-1,3-dioxolan-4-yl)methoxy]-ω-[(2-oxo-1,3-dioxolan-4-yl)methyl ]-poly[oxy(methyl-1,2-ethanediyl)] prepared in 1/and 105.3 g (1.44 moles, equivalent ratio amine to cyclic carbonate=1.1) of butylamine was charged in the same reactor as described in Example 1. The mixture was slowly heated to 70° C. Titration of the amine indicated that the reaction was complete after 3 h at 70° C. The amine excess was stripped at 70° C. for 3 hours.

A FTIR spectrum of the stripped product indicated the complete disappearance of the absorption band at 1797 cm$^{-1}$, characteristic of the carbonyl functions of the cyclic carbonate groups. $^1$H NMR indicated that the expected reaction occurred quantitatively to give a statistical mixture of the expected isomers (98% mol).

3/Acrylation of α-[3-hydroxy-2-[[(butylamino)carbonyl]oxy]propoxy]-ω-[3-[[((butylamino)carbonyl]oxy]-2-[hydroxypropyl]-poly[oxy(methyl-1,2-ethanediyl)] and isomers by transesterification Acrylation was then performed adding to the hydroxyalkyl carbamate prepared in 2/, 917.9 g (9.17 moles, equivalent ratio alkyl acrylate to hydroxyalkyl carbamate=7) ethyl acrylate, 2410 ppm on end product of BHT and 965 ppm on end product of PTZ. The reaction mixture was first dried by azeotropic distillation, as in Example 1. After adding 14.37 g zirconium n-butoxide (80% in butanol; Tyzor TNBZ manufactured by DuPont) and 13.28 g zirconium acetylacetonate (manufactured by Sachem; weight ratio of catalyst to the generated carbamoyloxy (meth)acrylate=0.04), the reaction mixture was maintained at 102-105° C. under air sparge and the ethanol generated was taken off overhead as a ethanol/ethyl acrylate azeotrope. The reaction was continued until a measure of the refractive index indicated that no more ethanol was present in the distillate. Reaction time was 11 hours.

After complete reaction, the catalyst was hydrolyzed by adding water (4.4 g per g catalyst) and stirring vigorously the mixture at 75° C. for 2 hour. After vacuum filtration on a diatomeceous earth bed and concentration/stripping (100 mmHg, 75° C., 3.5 hours), a product with 95% of the OH groups from the starting hydroxyalkylcarbamate being acrylated (according $^1$H NMR), and containing 1.5 ppm residual zirconium (according to atomic absorption spectrometry) was obtained.

Example 10

Preparation of poly[oxy(methyl-1,2-ethanediyl)], α-[3-[(1-oxo-2-propenyl)oxy]-2-[[(N-methylbutylamino)carbonyl]oxy]propoxy]-ω-[3-[[(N-methylbutylamino)carbonyl]oxy]-2-[(1-oxo-2-propenyl)oxy]propyl] and isomers with an average number of oxy(methyl-1,2-ethanediyl) units between 9 and 10

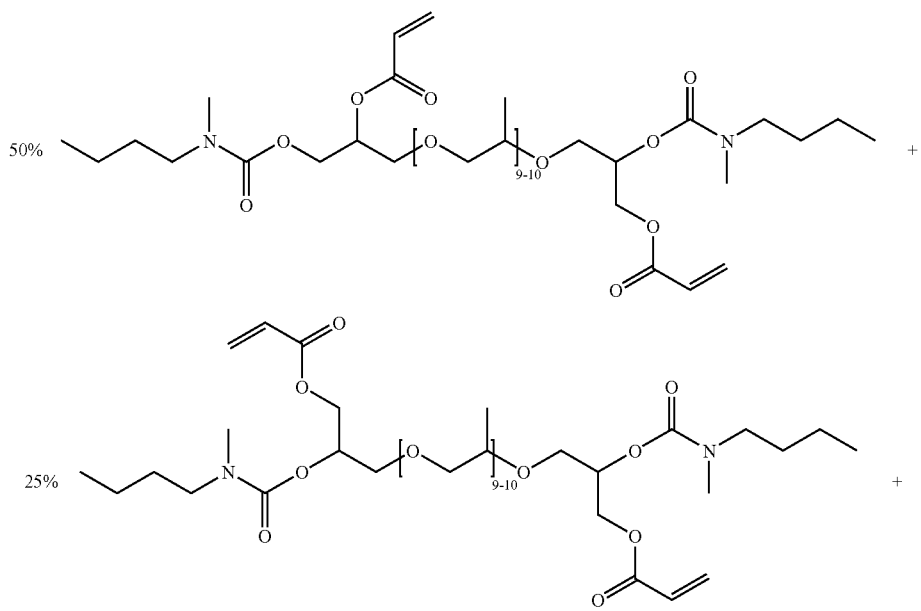

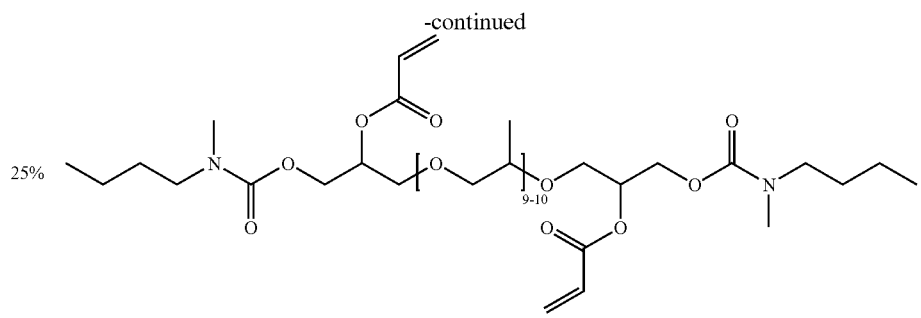

1/Preparation of poly[oxy(methyl-1,2-ethanediyl)], α-β-hydroxy-2-[[(N-methylbutylamino)carbonyl]oxy]propoxy]-ω-[3-[[(N-methylbutylamino)carbonyl]oxy]-2-[hydroxypropyl] and isomers with an average number of oxy(methyl-1,2-ethanediyl) units between 9 and 10.

α-[3-[(1-oxo-2-propenyl)oxy]-2-11(butylamino)carbonyl]oxy]propoxy]-ω-[3-[[(butylamino)carbonyl]oxy]-2-[(1-oxo-2-propenyl)oxy]propyl]-poly[oxy(methyl-1,2-ethanediyl)] from Example 9 was reacted using the same procedures and same stoichiometry as in Example 9, replacing butylamine by N-methylbutylamine.

2/Acrylation of poly[oxy(methyl-1,2-ethanediyl)], α-[3-hydroxy-2-[[(N-methylbutylamino)carbonyl]oxy]-ω-[3-[[(N-methylbutylamino)carbonyl]oxy]-2-[hydroxypropyl] and isomers by transesterification Same procedure with same stoichiometry was used as in Example 9.

Example 11

Preparation of poly[oxy(methyl-1,2-ethanediyl)], α-[3-[(1-oxo-2-propenyl)oxy]-2-[[[[[(1-oxo-2-propenyl)oxy]ethoxy]ethylamino]carbonyl]oxy]propoxy]-ω-[3-[[[[[(1-oxo-2-propenyl)oxy]ethoxy]ethylamino]carbonyl]oxy]-2-[(1-oxo-2propenyl)oxy]propyl] and isomers with an average number of oxy(methyl-1,2-ethanediyl) units between 9 and 10

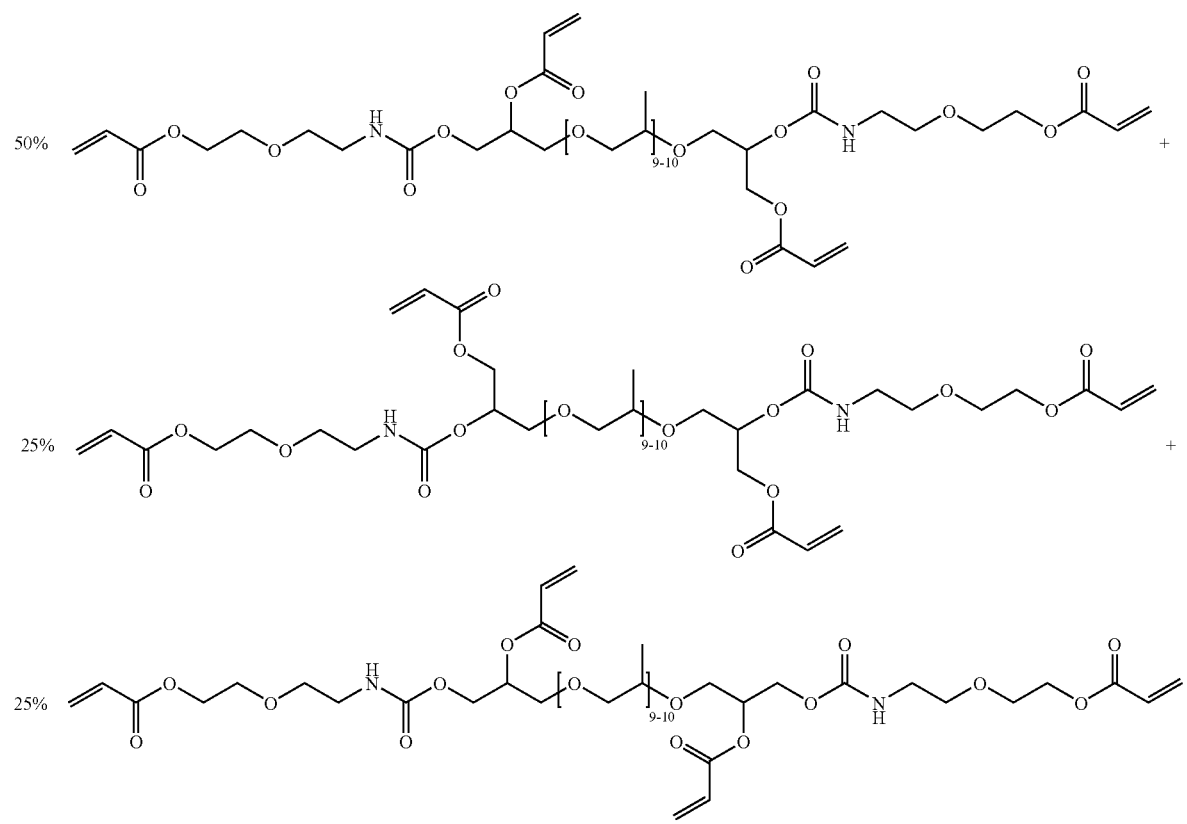

1/Preparation of poly[oxy(methyl-1,2-ethanediyl)], α-[3-hydroxy-2-[[[[[(1-oxo-2-propenyl)oxy]ethoxy]ethylamino]carbonyl]oxy]propoxy]-ω-[3-[[(N-methylbutylamino)carbonyl]oxy]-2-[hydroxypropyl] and isomers with an average number of oxy(methyl-1,2-ethanediyl) units between 9 and 10.

312.4 g of the α-[(2-oxo-1,3-dioxolan-4-yl)methoxy]-ω-[(2-oxo-1,3-dioxolan-4-yl)methyl]-poly[oxy(methyl-1,2-ethanediyl)] from Example 9 and 97.1 g (0.92 moles, equivalent ratio amine to cyclic carbonate=1.12) of 2-(2-aminoethoxyethanol) was charged in the same reactor as described in Example 1. The mixture was slowly heated to 80° C. Titration of the amine indicated that the reaction was complete after 5 h at 80° C.

Measurement of the hydroxyl content by titration (250 mg KOH/g) indicated that the expected reaction occurred quantitatively (theory: 239 mgKOH/g). Measurement of the ratio primary to secondary OH groups by $^{31}$P NMR after derivatization of the OH groups with chlorophospholane (0.67: 0.33), indicated a near-to-statistical mixture of the expected isomers (theory: 0.705:0.295).

2/Acrylation of poly[oxy(methyl-1,2-ethanediyl)], α-[3-hydroxy-2-[[[[[(1-oxo-2-propenyl)oxy]ethoxy]ethylamino]carbonyl]oxy]propoxy]-ω-[3-[[(N-methylbutylamino)carbonyl]oxy]-2-[hydroxypropyl] and isomers by transesterification Acrylation was then performed adding to the hydroxyalkyl carbamate prepared in 1/, 1202 g (12.0 moles, equivalent ratio alkyl acrylate to hydroxyalkyl carbamate=6) ethyl acrylate, 3600 ppm on end product of BHT and 1810 ppm on end product of PTZ. The reaction mixture was first dried by azeotropic distillation, as in Example 1. After adding 5.3 g zirconium n-butoxide (80% in butanol) and 4.9 g zirconium acetylacetonate (weight ratio of catalyst to the generated carbamoyloxy (meth)acrylate=0.02), the reaction mixture was maintained at 100-103° C. under air sparge and the ethanol generated was taken off overhead as a ethanol/ethyl acrylate azeotrope. The reaction was continued until a measure of the refractive index indicated that no more ethanol was present in the distillate. Reaction time was 7.5 hours.

After complete reaction, the catalyst was hydrolyzed by adding water (4 g per g catalyst) and stirring vigorously the mixture at 75° C. for 3 hours. After vacuum filtration on a diatomeceous earth bed and concentration/stripping (100 mmHg. 85° C., 2.5 hours), a product with 92% of the OH groups from the starting hydroxyalkylcarbamate being acrylated (according $^1$H NMR), and containing 2 ppm residual zirconium (according to atomic absorption spectrometry) was obtained.

The table here below gives the molecular weights (calculated from molecular formulae) and acrylate functionality as well as the measured viscosities of the undiluted products obtained from examples 6 to 11. Also given is the viscosity of CB 32 (commercial product supplied by Ackros), same product as Example 6 but obtained according to the isocyanate method by reacting 1 mole of trimethyl hexamethylene diisocyanate with 2 mole of HEA.

| Product | Theoretical Molecular weight (Dalton) | Acrylate Functionality | Höppler viscosity (25° C., mPa · s) |
| --- | --- | --- | --- |
| Example 6 | 442 | 2 | 7100 |
| CB 32 | 442 | 2 | 7010 |
| Example 7 | 429 | 2 | 11530 |
| Example 8 | 545 | 2 | 2150 |
| Example 9 | 984 | 2 | 1160 |
| Example 10 | 1016 | 2 | 495 |
| Example 11 | 1156 | 4 | 3370 |

The performances of coatings obtained from various formulations containing Example 6 and CB 32 have also been compared.

Formulations

| | F1 (parts) | F2 (parts) | F3 (parts) | F4 (parts) | F5 (parts) | F6 (parts) |
| --- | --- | --- | --- | --- | --- | --- |
| Example 6 | 70 | 70 | 70 | 0 | 0 | 0 |
| CB32 | 0 | 0 | 0 | 70 | 70 | 70 |
| HDDA | 30 | 0 | 0 | 30 | 0 | 0 |
| Ebecryl ® 160 (UCB Surface Specialties) | 0 | 30 | 0 | 0 | 30 | 0 |
| Genomer ® 1122 | 0 | 0 | 30 | 0 | 0 | 30 |
| Irgacure ® 500 (CibaGeigy) | 4 | 4 | 4 | 4 | 4 | 4 |
| Brookfield viscosity (25° C., mPa · s) | 285 | 1251 | 810 | 270 | 1206 | 804 |

Performances: 10 μm on Chamtenero 60 paper 80 W/cm, H bulb non focalised

| | F1 (parts) | F2 (parts) | F3 (parts) | F4 (parts) | F5 (parts) | F6 (parts) |
| --- | --- | --- | --- | --- | --- | --- |
| Reactivity: | | | | | | |
| Touch Dry (m/min) | 10 | 15 | 10 | 5 | 10 | 10 |
| Talc Dry (m/min) | 10 | 15 | 10 | 5 | 10 | 5 |
| Acetone Double Rubs (ADR) > 50 (m/min) | 45 | >80 | 45 | 35 | >80 | 35 |
| Cross-hatch Tape (TESA 4104) Adhesion | + | + | + | + | + | + |

-continued

| | F1 (parts) | F2 (parts) | F3 (parts) | F4 (parts) | F5 (parts) | F6 (parts) |
|---|---|---|---|---|---|---|
| (curing at 2 × 50 ADR) Chemical Resistance: | | | | | | |
| Distilled water | OK | OK | OK | OK | OK | OK |
| Ethanol (48% in water) | OK | OK | OK | OK | OK | OK |
| Ammonia (10%) | OK | OK | OK | OK | OK | OK |
| Oil (Paraffinum liquidum) | OK | OK | OK | OK | OK | OK |
| Scratch Resistance (steel wool) | 5× | 5× | 9× | 5× | 6× | 8× |

These results clearly show that the process according to the invention can lead to already-described urethane acrylates (Example 6) giving same or even slightly better coating properties as commercially-available products (CB 32) obtained using toxic raw materials.

They also clearly show that, when starting from multi-functional cyclic carbonates (Examples 8, 9 and 10), the process according to the invention leads to new urethane acrylates showing surprisingly much lower viscosity while having a similar (or even higher) molecular weight and a same functionality than already described products (CB 32). Using a secondary amine instead of a primary one for making the hydroxyalkyl carbamate can further lower the viscosity of the acrylate (Example 10 vs. Example 9).

Example 11 shows that the process according to the invention can lead to tetrafunctional urethane acrylate with an unprecedented low viscosity.

Example 12

Example 1 was repeated, except that a mixture of zirconium catalysts (11 grams of zirconium n-butoxide and acetylacetone (4 grams, manufactured by Wacker)) was used. The reaction was run at ambient pressure and after 4 hours the reaction mixture was cooled down and washed twice with water (12% w/w, 15% w/w $Na_2CO_3$ solution). After concentration under reduced pressure a clear, low colored (47 Apha), low viscous product (31 mPa·s) was obtained. Analysis showed the purity of the product was at least 95% w/w, containing less than 10 ppm Zr.

The invention claimed is:

1. Process for producing carbamoyloxy (meth)acrylates which comprises the transesterification of an hydroxyalkyl carbamate of formula (I), (II), (III), (IV), (V), (VI) or (VII)

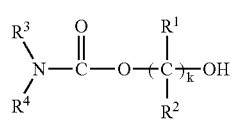
(I)

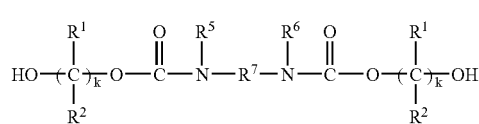
(II)

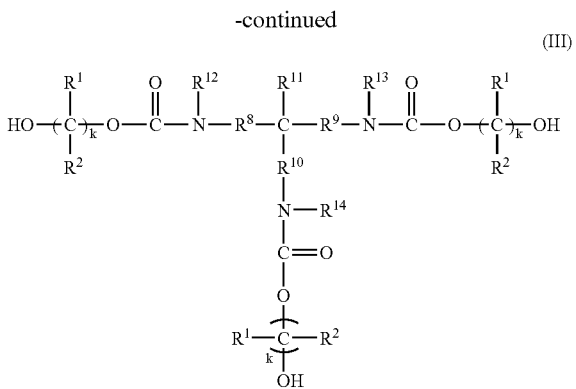
(III)

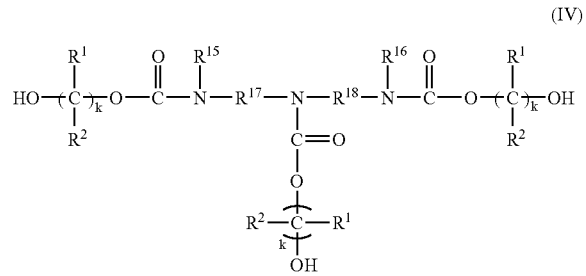
(IV)

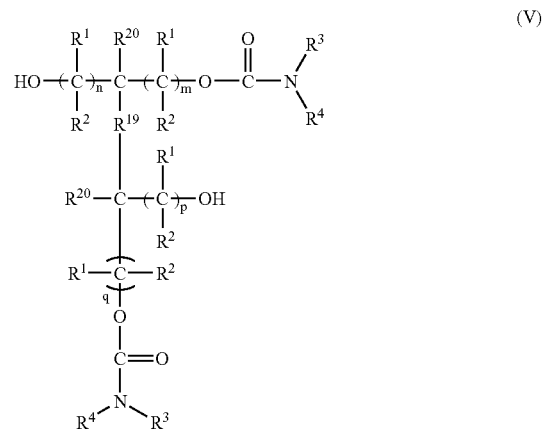
(V)

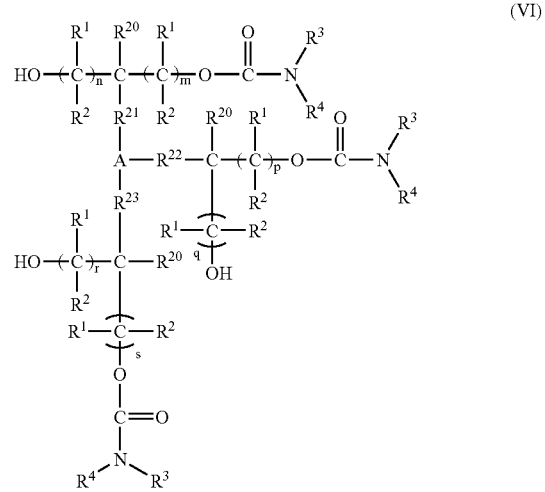
(VI)

-continued

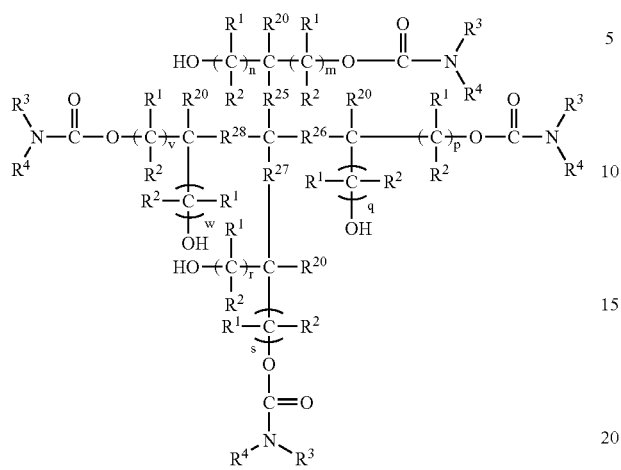
(VII)

wherein
k≧2
n=0 to 2
m=0 to 2
n+m≧1
p=n or m, q=n or m, r=n or m, s=n or m, v=n or m, w=n or m (p+q)=(r+s)=(v+w)=(n+m)
each $R^1$, each $R^2$, each $R^{20}$ is, independently, chosen from the group of
hydrogen,
halgen,
hydroxy,
alkyl, optionally substituted by hydroxy; halogen; aryl and/or aryl substituted by hydroxy, halogen or alkyl; and optionally containing from 1 to 8 ether bridges,
alkenyl, optionally substituted by hydroxy; halogen; aryl and/or aryl substituted by hydroxy, halogen or alkyl; and optionally containing from 1 to 8 ether bridges,
aryl, optionally substituted by hydroxy; halogen; alkyl; alkyl substituted by hydroxy, halogen and/or aryl; and/or alkyl containing from 1 to 8 ether bridges,
$R^3$ is an alkyl, optionally substituted by hydroxy, tertiary amine and/or aryl, and optionally containing from 1 to 20 ether bridges and/or from 1 to 3 tertiary amine bridges,
$R^4$, $R^5$, $R^6$, $R^{12}$, $R^{13}$, $R^{14}$, $R^{15}$ and $R^{16}$ are, independently, chosen from the group of
hydrogen, and
alkyl, optionally substituted by hydroxy, tertiary amine and/or aryl, and optionally containing from 1 to 8 ether bridges and/or from 1 to 3 tertiary amine bridges,
with the proviso that, respectively, $R^3$ and $R^4$, $R^5$ and $R^6$, $R^{12}$ and/or $R^{13}$ and/or $R^{14}$, $R^{15}$ and $R^{16}$ may be linked together in order to form a ring,
$R^7$, $R^8$, $R^9$, $R^{10}$, $R^{17}$ and $R^{18}$ are, independently, chosen from alkylene, alkenylene, arylene and aralkylene chains which may contain from 1 to 8 ether bridges and/or from 1 to 3 tertiary amine bridges,
$R^{11}$ is hydrogen or alkyl;

$R^{19}$, $R^{21}$, $R^{22}$, $R^{23}$, $R^{25}$, $R^{26}$, $R^{27}$ and $R^{28}$, are, independently, chosen from alkylene, alkenylene, arylene and aralkylene chains which may contain from 1 to 20 ether bridges, from 1 to 4 tertiary amine bridges, from 1 to 4 —CO— bridges and/or from 1 to 4 —O—CO— bridges;
A is

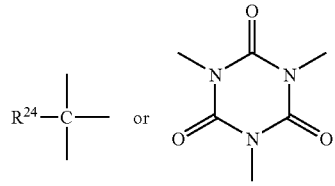

wherein $R^{24}$ is hydrogen or alkyl;
with an (meth)acrylate of formula (VIII)

$$CH_2=CR^{29}-COOR^{30}$$ (VIII)

wherein $R^{29}$ is hydrogen or methyl, and $R^{30}$ represents an alkyl group comprising from 1 to 8 carbon atoms; in an equivalent ratio of (meth)acrylate to hydroxyalkyl carbamate higher than 3.5 and in the presence of an organotitanate, an organozirconate or an organotin catalyst.

2. The process according to claim 1, wherein the hydroxyalkyl carbamates of formula (I), (II), (III) and (IV) are obtained by reacting amines of, respectively, formula (IX), (X), (XI) and (XII)

(IX)

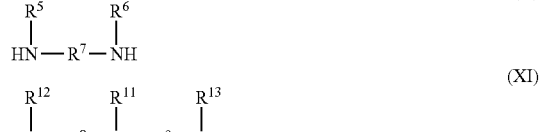
(X)

(XI)

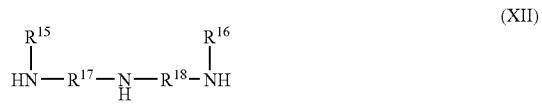
(XII)

wherein $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$, are defined as in claim 1, with a cyclic carbonate of formula (XIII)

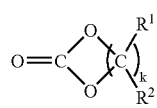
(XIII)

wherein $R^1$, $R^2$ and k are defined as in claim 1.

3. The process according to claim 1, wherein the hydroxyalkyl carbamates of formula (V), (VI) and (VII) are obtained by reacting an amine of formula (IX)

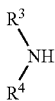

(IX)

wherein $R^3$ and $R^4$ are defined as in claim 1, with, respectively, a cyclic carbonate of formula (XIV), (XV) and (XVI)

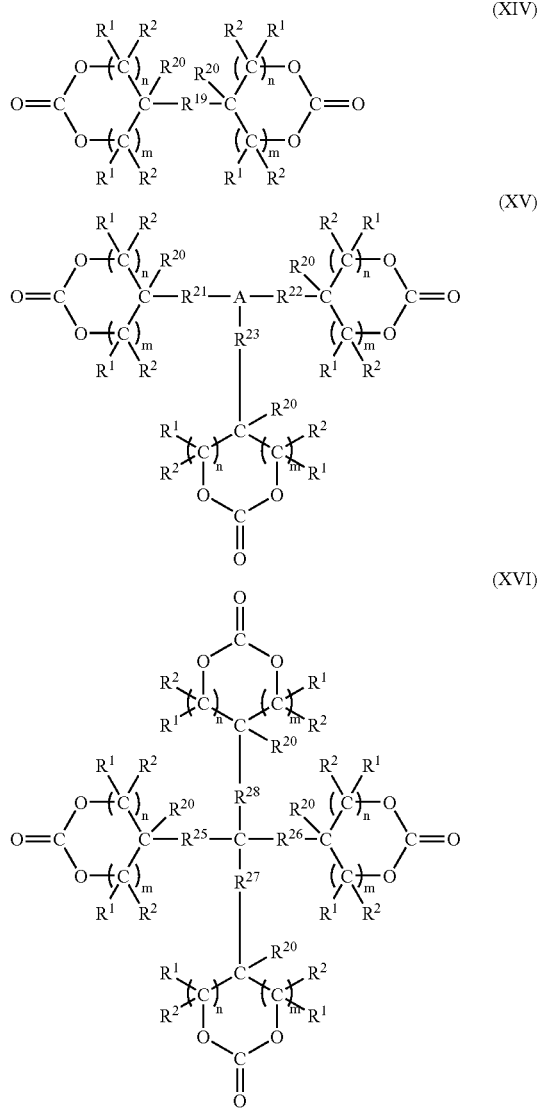

wherein $R^1$, $R^2$, $R^{19}$, $R^{20}$, $R^{21}$, $R^{22}$, $R^{23}$, $R^{24}$, $R^{25}$, $R^{26}$, $R^{27}$, $R^{28}$, A, n and m are defined as in claim 1.

4. Process according to claim 1, wherein $R^{30}$ is methyl, ethyl or n-butyl.

5. Process according to claim 1, wherein the equivalent ratio of (meth)acrylate to the hydroxyalkyl carbamate is at least 4.

6. Process according to claim 1, wherein the catalyst is an alkyltitanate wherein each alkyl, independently, comprises from 2 to 8 carbon atoms or an alkylzirconate wherein each alkyl, independently, comprises from 2 to 8 carbon atoms or a zirconium 1,3-diketone chelate or a mixture thereof.

7. Process according to claim 1, wherein the transesterification reaction is conducted in the presence of at least one polymerization inhibitior.

8. Process according to claim 7, wherein the polymerization inhibitor is chosen from sterically hindered phenol derivatives.

9. Process according to claim 8, wherein sterically hindered phenolic inhibitor is selected from the group of 2,6-di-tert-butyl-4-methylphenol (BHT), 2,6-dimethylphenol, 2,2'-methylenebis(4-methyl-6-(1-methyl-cyclohexyl) phenol), 2,2'-methylenebis(4-methyl-6-tert-butylphenol), 2,2'-methylenebis(4-ethyl-6-tert-butylphenol), 2,4-dimethyl-6-(1-methylpentadecyl)-phenol, alpha-tocopherol (vitamin E) and their mixtures.

10. Process according to claim 8, wherein the concentration of the sterically hindered phenol is from 100 to 5000 ppm w/w based on the quantity of carbamoyloxy (meth) acrylate formed.

11. Process according to claim 7, wherein at least 100 ppm of a non-phenolic polymerization inhibitor is added during the transesterification reaction.

12. Process according to claim 1, wherein the temperature during the transesterifcation reaction is at most 110° C.

13. Process according to claim 1, wherein the temperature during the transesterification reaction is at most 75° C. when hydroxyalkyl carbamates bearing only primary hydroxy group(s) and alkyltitanate catalysts are used.

14. Process according to claim 1, wherein the weight ratio of catalyst to the generated carbamoyloxy (meth)acrylate is from 0.003 to 0.1.

15. Process according to claim 1, wherein the reaction mixture obtained after the transesterifaction is treated with water and/or with a polyol.

16. Process according to claim 1, wherein k=2 or 3 and n+m, p+q, r+s, v+w=1.

17. Process according to claim 1, wherein in formula (I), (II), (III) and (IV) one of the $R^1$ substituents is chosen from the group of hydrogen, methyl, ethyl, hydroxymethyl, chloromethyl, allyloxymethyl, the $R^2$ substituent present on the same substituent as said $R^1$ subtituent is chosen from hydrogen and methyl, and all other $R^1$ and $R^2$ substituents are hydrogen.

18. Process according to claim 1, wherein in formula (V), (VI) and (VII) each $R^1$, each $R^2$ and each $R^{20}$ is hydrogen.

19. Process according to claim 1, wherein in formula (I), (V), (VI) and (VII) and (IX) $R^4$ is hydrogen and $R^3$ is an alkyl comprising at least 3 carbon atoms and substitued by at least one hydroxy and optionally containing one or two ether bridges.

* * * * *